(12) United States Patent
Tiberghien et al.

(10) Patent No.: US 11,352,324 B2
(45) Date of Patent: Jun. 7, 2022

(54) METHODS

(71) Applicant: MEDIMMUNE LIMITED, Cambridge (GB)

(72) Inventors: Arnaud Charles Tiberghien, Cambridge (GB); Andrew Duncan Campbell, Macclesfield (GB); Jeremy Parker, Macclesfield (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 16/977,072

(22) PCT Filed: Mar. 1, 2019

(86) PCT No.: PCT/EP2019/055116
§ 371 (c)(1),
(2) Date: Aug. 31, 2020

(87) PCT Pub. No.: WO2019/166615
PCT Pub. Date: Sep. 6, 2019

(65) Prior Publication Data
US 2020/0399215 A1 Dec. 24, 2020

(30) Foreign Application Priority Data

Mar. 1, 2018 (GB) .................................... 1803342

(51) Int. Cl.
*C07D 207/20* (2006.01)
(52) U.S. Cl.
CPC .................. *C07D 207/20* (2013.01)
(58) Field of Classification Search
None
See application file for complete search history.

(56) References Cited

U.S. PATENT DOCUMENTS

| | | |
|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |

(Continued)

FOREIGN PATENT DOCUMENTS

| | | |
|---|---|---|
| CN | 101171257 | 4/2008 |
| EP | 0522868 | 1/1993 |

(Continued)

OTHER PUBLICATIONS

Adair et al., "Antibody-drug conjugates—a perfect synergy," Exp. Opin. Biol. Ther. (2012), pp. 1-16.
Adams et al., "Molecular modelling of a sequence-specific DNA-binding agent based on the pyrrolo[2,1-c][1,4]benzodiazepines," Pharm. Pharmacol. Commun. (1999) 5:555-560.

(Continued)

*Primary Examiner* — Samantha L Shterengarts
(74) *Attorney, Agent, or Firm* — Casimir Jones S.C.; Lisa Mueller

(57) ABSTRACT

A method of synthesising a compound of formula (I): (I) from a compound of formula (II): (II) where $R^8$ is either: (i) $Prot^{O3}$; or (ii) a group of formula (A1) in formula (I) and (A2) in formula (II): (A1), (A2).

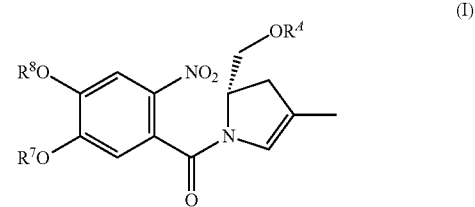

(I)

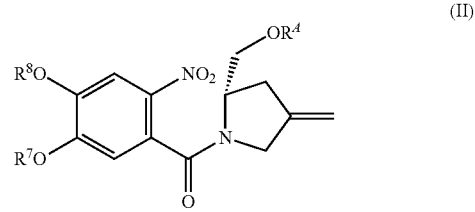

(II)

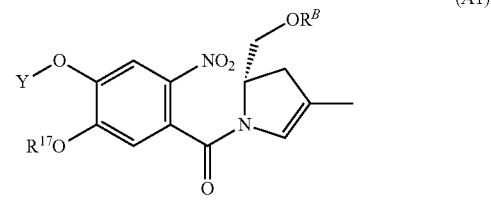

(A1)

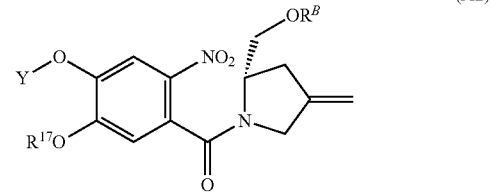

(A2)

18 Claims, No Drawings

(56) References Cited

U.S. PATENT DOCUMENTS

| | | |
|---|---|---|
| 4,816,567 A | 3/1989 | Cabilly et al. |
| 4,923,984 A | 5/1990 | Matsumura et al. |
| 5,362,852 A | 11/1994 | Geoghegan |
| 5,418,241 A | 5/1995 | Jegham et al. |
| 5,440,021 A | 8/1995 | Chuntharapai et al. |
| 5,561,119 A | 10/1996 | Jacquesy et al. |
| 5,583,024 A | 12/1996 | McElroy et al. |
| 5,621,002 A | 4/1997 | Bosslet et al. |
| 5,644,033 A | 7/1997 | Seon |
| 5,674,713 A | 10/1997 | McElroy et al. |
| 5,700,670 A | 12/1997 | Yamagishi et al. |
| 5,773,223 A | 6/1998 | Shyamala et al. |
| 5,792,616 A | 8/1998 | Persico et al. |
| 5,854,399 A | 12/1998 | Salomon et al. |
| 5,869,445 A | 2/1999 | Cheever et al. |
| 5,976,551 A | 11/1999 | Mottez et al. |
| 6,011,146 A | 1/2000 | Mottez et al. |
| 6,153,408 A | 11/2000 | Abastado et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,362,331 B1 | 3/2002 | Kamal et al. |
| 6,518,404 B1 | 2/2003 | Li et al. |
| 6,534,482 B1 | 3/2003 | Fikes et al. |
| 6,555,339 B1 | 4/2003 | Liaw et al. |
| 6,562,806 B1 | 5/2003 | Thurston et al. |
| 6,602,677 B1 | 8/2003 | Wood et al. |
| 6,608,192 B1 | 8/2003 | Thurston et al. |
| 6,660,742 B2 | 12/2003 | Lee |
| 6,660,856 B2 | 12/2003 | Wang |
| 6,677,435 B2 | 1/2004 | Barbas, III et al. |
| 6,747,144 B1 | 6/2004 | Thurston et al. |
| 6,759,509 B1 | 7/2004 | King et al. |
| 6,835,807 B1 | 12/2004 | Sasaki et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,223,837 B2 | 5/2007 | De Groot et al. |
| 7,244,724 B2 | 7/2007 | Liu et al. |
| 7,265,105 B2 | 9/2007 | Thurston et al. |
| 7,375,078 B2 | 5/2008 | Feng |
| 7,407,951 B2 | 8/2008 | Thurston et al. |
| 7,429,658 B2 | 9/2008 | Howard et al. |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,723,485 B2 | 5/2010 | Junutula et al. |
| 7,741,319 B2 | 6/2010 | Howard et al. |
| 8,034,808 B2 | 11/2011 | Delavault et al. |
| 8,163,736 B2 | 4/2012 | Gauzy et al. |
| 8,321,774 B2 | 11/2012 | Barthal et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 9,242,013 B2 | 1/2016 | Howard et al. |
| 9,321,774 B2 | 4/2016 | Howard et al. |
| 9,376,440 B2 | 6/2016 | Howard et al. |
| 9,387,259 B2 | 7/2016 | Jeffrey et al. |
| 9,388,187 B2 | 7/2016 | Howard et al. |
| 9,399,073 B2 | 7/2016 | Howard et al. |
| 9,399,641 B2 | 7/2016 | Howard et al. |
| 9,415,117 B2 | 8/2016 | Howard |
| 9,464,141 B2 | 10/2016 | Asundi et al. |
| 9,526,798 B2 | 12/2016 | Jeffrey et al. |
| 9,562,049 B2 | 2/2017 | Howard |
| 9,592,240 B2 | 3/2017 | Howard et al. |
| 9,624,227 B2 | 4/2017 | Howard et al. |
| 9,649,390 B2 | 5/2017 | Howard et al. |
| 9,707,301 B2 | 7/2017 | Jeffrey et al. |
| 9,713,647 B2 | 7/2017 | Jeffrey et al. |
| 9,732,084 B2 | 8/2017 | Howard et al. |
| 9,745,303 B2 | 8/2017 | Howard et al. |
| 9,889,207 B2 | 2/2018 | Howard |
| 9,956,298 B2 | 5/2018 | Howard et al. |
| 2001/0055751 A1 | 12/2001 | Reiter et al. |
| 2002/0034749 A1 | 3/2002 | Billing-Medel et al. |
| 2002/0042366 A1 | 4/2002 | Thompson et al. |
| 2002/0150573 A1 | 10/2002 | Nussenzweig |
| 2002/0193567 A1 | 12/2002 | Jacobs et al. |
| 2003/0060612 A1 | 3/2003 | Goddard et al. |
| 2003/0062401 A1 | 4/2003 | Hasz et al. |
| 2003/0064397 A1 | 4/2003 | Spancake et al. |
| 2003/0065143 A1 | 4/2003 | Eaton et al. |
| 2003/0091580 A1 | 5/2003 | Mitcham et al. |
| 2003/0096743 A1 | 5/2003 | Senter et al. |
| 2003/0096961 A1 | 5/2003 | Baker et al. |
| 2003/0105292 A1 | 6/2003 | Liaw et al. |
| 2003/0109676 A1 | 6/2003 | Li et al. |
| 2003/0118592 A1 | 6/2003 | Ledbetter et al. |
| 2003/0119121 A1 | 6/2003 | Baker et al. |
| 2003/0119122 A1 | 6/2003 | Baker et al. |
| 2003/0119125 A1 | 6/2003 | Baker et al. |
| 2003/0119126 A1 | 6/2003 | Baker et al. |
| 2003/0119128 A1 | 6/2003 | Baker et al. |
| 2003/0119129 A1 | 6/2003 | Baker et al. |
| 2003/0119130 A1 | 6/2003 | Baker et al. |
| 2003/0119131 A1 | 6/2003 | Baker et al. |
| 2003/0124140 A1 | 7/2003 | Bangur et al. |
| 2003/0124579 A1 | 7/2003 | Mack et al. |
| 2003/0129192 A1 | 7/2003 | Chenault et al. |
| 2003/0130189 A1 | 7/2003 | Senter et al. |
| 2003/0134790 A1 | 7/2003 | Langenfeld |
| 2003/0143557 A1 | 7/2003 | Penner |
| 2003/0157089 A1 | 8/2003 | Xu et al. |
| 2003/0165504 A1 | 9/2003 | Retter et al. |
| 2003/0175775 A1 | 9/2003 | Lepoul et al. |
| 2003/0185830 A1 | 10/2003 | Xu et al. |
| 2003/0186372 A1 | 10/2003 | Baker et al. |
| 2003/0186373 A1 | 10/2003 | Baker et al. |
| 2003/0194704 A1 | 10/2003 | Penn et al. |
| 2003/0195196 A1 | 10/2003 | Thurston et al. |
| 2003/0206918 A1 | 11/2003 | Fanger et al. |
| 2003/0219806 A1 | 11/2003 | Glucksmann et al. |
| 2003/0224411 A1 | 12/2003 | Stanton et al. |
| 2003/0224454 A1 | 12/2003 | Ryseck et al. |
| 2003/0228319 A1 | 12/2003 | Frantz et al. |
| 2003/0232056 A1 | 12/2003 | Fanger et al. |
| 2003/0232350 A1 | 12/2003 | Afar et al. |
| 2004/0001827 A1 | 1/2004 | Dennis |
| 2004/0005320 A1 | 1/2004 | Thompson et al. |
| 2004/0005538 A1 | 1/2004 | Chen et al. |
| 2004/0005563 A1 | 1/2004 | Mack et al. |
| 2004/0005598 A1 | 1/2004 | Devaux et al. |
| 2004/0018194 A1 | 1/2004 | Francisco et al. |
| 2004/0018553 A1 | 1/2004 | Billing-Medel et al. |
| 2004/0022727 A1 | 2/2004 | Stanton et al. |
| 2004/0044179 A1 | 3/2004 | Baker et al. |
| 2004/0044180 A1 | 3/2004 | Baker et al. |
| 2004/0052793 A1 | 3/2004 | Carter et al. |
| 2004/0101874 A1 | 5/2004 | Ghosh et al. |
| 2004/0101899 A1 | 5/2004 | Dillon et al. |
| 2004/0121940 A1 | 6/2004 | De Groot et al. |
| 2004/0138269 A1 | 7/2004 | Sun et al. |
| 2004/0197325 A1 | 10/2004 | Law et al. |
| 2004/0198722 A1 | 10/2004 | Thurston et al. |
| 2004/0249130 A1 | 12/2004 | Stanton et al. |
| 2005/0271615 A1 | 12/2005 | Shabat et al. |
| 2006/116422 A1 | 6/2006 | De Groot et al. |
| 2007/0072846 A1 | 3/2007 | Vishnuvajjala et al. |
| 2007/0092940 A1 | 4/2007 | Eigenbrot et al. |
| 2007/0154906 A1 | 7/2007 | Martin et al. |
| 2007/0185336 A1 | 8/2007 | Rossen et al. |
| 2007/0191349 A1 | 8/2007 | Howard et al. |

(56) References Cited

U.S. PATENT DOCUMENTS

| | | |
|---|---|---|
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0112961 A1 | 5/2008 | Stavenhagen et al. |
| 2008/0206239 A1 | 8/2008 | Jones et al. |
| 2008/0213289 A1 | 9/2008 | Francisco et al. |
| 2008/0214525 A1 | 9/2008 | Howard et al. |
| 2009/0036431 A1 | 2/2009 | Gauzy et al. |
| 2009/0148942 A1 | 6/2009 | McDonagh et al. |
| 2009/0149449 A1 | 6/2009 | Liu et al. |
| 2009/0274713 A1 | 11/2009 | Chari et al. |
| 2009/0304710 A1 | 12/2009 | Park et al. |
| 2010/0028346 A1 | 2/2010 | Lutz et al. |
| 2010/0047257 A1 | 2/2010 | Blanc et al. |
| 2010/0113425 A1 | 5/2010 | Howard et al. |
| 2010/0203007 A1 | 8/2010 | Li et al. |
| 2010/0316656 A1 | 12/2010 | Bouchard et al. |
| 2011/0039969 A1 | 2/2011 | Muratoglu et al. |
| 2011/0070227 A1 | 3/2011 | Novotney-Barry et al. |
| 2011/0091372 A1 | 4/2011 | Ghayur et al. |
| 2011/0160192 A1 | 6/2011 | Howard et al. |
| 2011/0195021 A1 | 8/2011 | Deckert et al. |
| 2011/0195022 A1 | 8/2011 | Deckert et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2012/0233172 A1 | 9/2012 | Skillcorn et al. |
| 2012/0238731 A1 | 9/2012 | Fishkin et al. |
| 2013/0028917 A1 | 1/2013 | Howard et al. |
| 2013/0028919 A1 | 1/2013 | Howard et al. |
| 2013/0137659 A1 | 5/2013 | Commercon et al. |
| 2013/0244171 A1 | 9/2013 | Yamasaki et al. |
| 2013/0266595 A1 | 10/2013 | Flygare et al. |
| 2013/0266596 A1 | 10/2013 | Li et al. |
| 2013/0302359 A1 | 11/2013 | Li et al. |
| 2013/0304357 A1 | 11/2013 | Koci et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0088089 A1 | 3/2014 | Chari |
| 2014/0120118 A1 | 5/2014 | Howard |
| 2014/0121126 A1 | 5/2014 | Bivona et al. |
| 2014/0127239 A1 | 5/2014 | Howard |
| 2014/0155590 A1 | 6/2014 | Commercon et al. |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |
| 2016/0075787 A1 | 3/2016 | Zheng et al. |
| 2016/0144052 A1 | 5/2016 | Howard et al. |
| 2016/0074527 A1 | 7/2016 | Flygare et al. |
| 2016/0250344 A1 | 9/2016 | Howard et al. |
| 2016/0250345 A1 | 9/2016 | Howard et al. |
| 2016/0250346 A1 | 9/2016 | Howard et al. |
| 2016/0256561 A1 | 9/2016 | Howard et al. |
| 2016/0263242 A1 | 9/2016 | Howard et al. |
| 2016/0310611 A1 | 10/2016 | Flygare et al. |
| 2017/0239365 A1 | 8/2017 | Howard et al. |
| 2017/0290924 A1 | 10/2017 | Jeffrey et al. |
| 2017/0298137 A1 | 10/2017 | Jeffrey et al. |
| 2017/0340752 A1 | 11/2017 | Howard |
| 2018/0125997 A1 | 5/2018 | Howard et al. |
| 2018/0134717 A1 | 5/2018 | Howard et al. |

FOREIGN PATENT DOCUMENTS

| | | |
|---|---|---|
| EP | 0875569 | 11/1998 |
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| EP | 3690038 A1 | 8/2020 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |

(56) References Cited

FOREIGN PATENT DOCUMENTS

| | | |
|---|---|---|
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006065533 A2 | 6/2006 |
| WO | WO 2006111759 | 10/2006 |
| WO | WO 2007039752 | 4/2007 |

(56) References Cited

FOREIGN PATENT DOCUMENTS

| | | |
|---|---|---|
| WO | WO 2007044515 | 4/2007 |
| WO | WO 2007085930 | 8/2007 |
| WO | WO 2008010101 | 1/2008 |
| WO | WO 2008022152 | 2/2008 |
| WO | WO 2008047242 | 4/2008 |
| WO | WO 2008050140 | 5/2008 |
| WO | WO 2008070593 | 6/2008 |
| WO | WO 2009016516 | 2/2009 |
| WO | WO 2009052249 | 4/2009 |
| WO | WO 2009060208 | 5/2009 |
| WO | WO 2009060215 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010095031 | 8/2010 |
| WO | WO 2011023883 | 3/2011 |
| WO | WO 2011038159 | 3/2011 |
| WO | WO 2011059850 | 5/2011 |
| WO | WO 2011100227 | 8/2011 |
| WO | WO 2011128650 | 10/2011 |
| WO | WO 2011130598 | 10/2011 |
| WO | WO 2011130613 | 10/2011 |
| WO | WO 2011130615 | 10/2011 |
| WO | WO 2011130616 | 10/2011 |
| WO | WO 2011133039 | 10/2011 |
| WO | WO 2012014147 | 2/2012 |
| WO | WO 2012018325 | 2/2012 |
| WO | WO 2012039717 | 3/2012 |
| WO | WO 2012064733 | 5/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053872 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013164592 | 11/2013 |
| WO | WO 2013164593 | 11/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO 2014031566 | 2/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014080251 | 5/2014 |
| WO | WO 2014096365 | 6/2014 |
| WO | WO 2014096368 | 6/2014 |
| WO | WO 2014130879 | 8/2014 |
| WO | WO 2014140174 | 9/2014 |
| WO | WO 2014140862 | 9/2014 |
| WO | WO 2014159981 | 10/2014 |
| WO | WO 2014174111 | 10/2014 |
| WO | WO 2015028850 | 3/2015 |
| WO | WO 2015031693 | 3/2015 |
| WO | WO 2015052321 | 4/2015 |
| WO | WO 2015052322 | 4/2015 |
| WO | WO 2015052332 | 4/2015 |
| WO | WO 2015052333 | 4/2015 |
| WO | WO 2015052334 | 4/2015 |
| WO | WO 2015052335 | 4/2015 |
| WO | WO 2015052532 | 4/2015 |
| WO | WO 2015052533 | 4/2015 |
| WO | WO 2015052534 | 4/2015 |
| WO | WO 2015052535 | 4/2015 |
| WO | WO 2015095124 | 6/2015 |
| WO | WO 2015112822 | 7/2015 |
| WO | WO 2015157595 | 10/2015 |
| WO | WO 2015159076 | 10/2015 |
| WO | WO 2016201065 | 12/2015 |
| WO | WO 2016037644 | 3/2016 |
| WO | WO 2016040868 | 3/2016 |
| WO | WO 2016044560 | 3/2016 |
| WO | WO 2016053107 | 4/2016 |
| WO | WO 2016166297 | 10/2016 |
| WO | WO 2016166298 | 10/2016 |
| WO | WO 2016166299 | 10/2016 |
| WO | WO 2016166300 | 10/2016 |
| WO | WO 2016166302 | 10/2016 |
| WO | WO 2016166305 | 10/2016 |
| WO | WO 2016166307 | 10/2016 |
| WO | WO 2017035353 | 3/2017 |
| WO | WO 2017059289 | 4/2017 |
| WO | WO 2017137553 | 8/2017 |
| WO | WO 2017186894 | 11/2017 |
| WO | WO 2017201132 | 11/2017 |
| WO | WO 2018031662 | 2/2018 |
| WO | WO 2018182341 | 10/2018 |
| WO | WO 2020006722 | 1/2020 |

OTHER PUBLICATIONS

Aird et al., "ABCB1 genetic polymorphism influences the pharmacology of the new pyrrolobenzodiazepine derivative SJG-136," Pharmacogenomics Journal (2008) 8(4):289-296.

Alley et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-lmmolative Dendrimers," (2003) Angew. Chem. Int. Ed. 42:4494-4499.

Amsberry, et al., "The Lactonization of 2'-Hydroxyhydrocinnamic Acid Amides: A Potential Prodrug for Amines," (1990) J. Org. Chem. 55:5867-5877.

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.

Antonow, D. et al., "Synthesis of DNA-Interactive Pyrrolo [2,1-c][1,4] benzodiazepines (PBDs)" Chemical Reviews, 2011, 111 (4):2815-2864.

Antonow, D. et al.,"Parallel synthesis of a novel C2-aryl pyrrolo[2,1-c][1,4]benzodiazepine (PBD) library," J. Comb. Chem. (2007) 9:437-445.

Arai H., et al., "Molecular cloning of human endothelin receptors and their expression in vascular endothelial cells and smooth muscle cells," Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

(56) References Cited

OTHER PUBLICATIONS

Arima et al., "Studies on Tomaymycin, a New Antibiotic. I. Isolation and Properties of Tomaymycin," J. Antibiotics (1972) 25:437-444.
Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.
Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).
Attie T., et al., "Mutation of the endothelin-receptor B gene in Waardenburg-Hirschsprung disease," Hum. Mol. Genet. 4, 2407-2409, 1995.
Auricchio A., et al., "Endothelin-B receptor mutations in patients with isolated Hirschsprung disease from a non-inbred population," Hum. Mol. Genet. 5:351-354, 1996.
Axup et al., "Synthesis of site-specific antibody-drug conjugates using unnatural amino acids." Proc Natl Acad Sci U S A. Oct. 2, 2012; 109(40):16101-6.
Bahrenberg et al., "Reduced Expression of PSCA, a Member of the LY-6 Family of Cell Surface Antigens, in Bladder, Esophagus, and Stomach Tumors," Biochem. Biophys. Res. Commun. (2000) 275(3):783-788.
Banker, G.S. et al., "Modern Pharmaceutics", Third edition, Marcel Dekker, New York (1996) 451 and 596.
Barel M., et al., "Evidence for a new transcript of the Epstein-Barr virus/C3d receptor (CR2, CD21) which is due to alternative exon usage," Mol. Immunol. 35, 1025-1031, 1998.
Barella et al., "Sequence variation of a novel heptahelical leucocyte receptor through alternative transcript formation," (1995) Biochem. J. 309:773-779.
Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.
Batisse, et al., "A new delivery system for Auristatin in STxB-drug conjugate therapy." European J. Medicinal Chemistry, 2015, 95: 483-491.
Beck et al., "DNA Sequence Analysis of 66 kb of the Human MHC Class II Region Encoding a Cluster of Genes for Antigen Processing," (1992) J. Mol. Biol. 228:433-441.
Beck et al., "Evolutionary Dynamics of Non-coding Sequences Within the Class II Region of the Human MHC," (1996) J. Mol. Biol. 25 255:1-13.
Berge et al., "Pharmaceutical Salts," J. Pharm. Sci. (1977) 66:1-19.
Berry, J. M. et al., "Solid-phase synthesis of DNA-interactive pyrrolo[2,1-c][1,4]benzodiazepines," Tetrahedron Letters (2000) 41:6171-6174.
Berry, J.M. et al., "Synthesis and biological evaluation of an N10-Psec substituted pyrrolo[2,1-c][1,4]benzodiazepine prodrug," Bioorg. Med. Chem. Lett. (2002) 12:1413-1416.
Bien & Balcerska, "Serum Soluble Interleukin 2 receptor in human cancer of adults and children: a review," Biomarkers, 2008, 13(1): 1-26.
Blanc et al., "SAR3419: an anti-CD19-Maytansinoid Immunoconjugate for the treatment of B-cell malignancies," Clin Cancer Res., 2011, 17(20):6448-58.
Blumberg H., et al., "Interleukin 20: Discovery, Receptor Identification, and Role in Epidermal Function," Cell 104, 9-19, 2001.
Bose et al., "New Approaches to Pyrrolo[2,1-c][1,4]benzodiazepines: Synthesis, DNA-binding and cytotoxicity of DC-81," Tetrahedron, 48, 751-758 (1992).
Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.
Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).
Bourgeois C., et al., "Endothelin-1 and ETA Receptor Expression in Vascular Smooth Muscle Cells from Human Placenta: A New ETA Receptor Messenger Ribonucleic Acid is Generated by Alternative Splicing of Exon 3," J. Clin. Endocrinol. Metab. 82, 3116-3123, 1997.
Brand et al., Prospect for anti-HER2 receptor therapy in breast cancer. Anticancer Res. Jan.-Feb. 2006;26(1B):463-70.
Brinster et al., "Introits increase transcriptional efficiency in transgenic mice," (1988) Proc. Natl. Acad. Sci. USA 85:836-840.
Buchman et al., "Comparison of Intron-Dependent and Intron-Independent Gene Expression," (1988) Mol. Cell. Biol. 8:4395-4405.
Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.
Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.
Burke, P.J. et al., "Novel immunoconjugates comprised of streptonigrin and 17-amino-geldanamycin attached via a dipeptide-p-aminobenzyl-amine linker system," Bioorg. Med. Chem. Lett., Apr. 2009, 19(10):2650-2653.
Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.
Carl et al., "A Novel Connector Linkage Applicable in Prodrug Design," (1981) J. Med. Chem. 24:479-480.
Carlsson et al., "Protein Thiolation and Reversible Protein-Protein Conjugation," (1978) Biochem. J. 173:723-737.
Carter, P., "Potent antibody therapeutics by design," (2006) Nature Reviews Immunology 6:343-357.
Casset et al., "A peptide mimetic of an anti-CD4 monoclonal antibody by rational design." Biochem Biophys Res Commun. Jul. 18, 2003; 307(1):198-205.
CellTiter-Glo Luminescent Cell Viability Assay, Promega Corp. Technical Bulletin TB288, dated Jan. 13, 2012 (14 pages).
Chakravarty et al., "Plasmin-Activated Prodrugs for Cancer Chemotherapy. 2. Synthesis and Biological Activity of Peptidyl Derivatives of Doxorubicin," (1983) J. Med. Chern. 26:638-644.
Chan, J. and Watt, V.M., "eek and erk, new members of the eph subclass of receptor protein-tyrosine kinases," Oncogene 6 (6), 1057-1061 (1991).
Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).
Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.
Cheung, A., "Direct liquid chromatography determination of the reactive imine SJG-136 (NSC 694501)," J. Chromat. B: Anal. Techn. Biomed. Life Sci. (2005) 822(1-2):10-20.
Child et al., "Translational Control by an Upstream Open Reading Frame in the HER-2/neu Transcript," (1999) J. Bioi. Chern. 274: 24335-24341.
Cho et al., "Structure of the extracellular region of HER2 alone and in complex with the Herceptin Fab," Nature 421, 756-760, 2003.
Ciccodicola, A , et al., "Molecular characterization of a gene of the 'EGF family' expressed in undifferentiated human NTERA2 teratocarcinoma cells," EMBO J. 8 (7):1987-1991 (1989).
Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.
Clackson et al., "Making antibody fragments using phage display libraries," (1991) Nature, 352:624-628.

(56) References Cited

OTHER PUBLICATIONS

Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.
Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.
Clingen, P.H., "the XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.
Clinical Trial, "Translational research: 4 ways to fix the clinical trial." 2011, http://www.nature.com/news/2011/110928/full/477526a.html.
Clinical Trials Identifier NCT02034227, Safety, Tolerability Study of SG2000 in the Treatment of Advanced Chronic Lymphocytic Leukemia and Acute Myeloid Leukemia [online] NIH U.S. National Library of Medicine 2014 [Retrieved on Nov. 4, 2020], Retrieved from the Internet: <https://www.clinicaltrials.gov/ct2/show/NCT02034227>.
Collins, "Generation and initial analysis of more than 15,000 full-length human and mouse eDNA sequences," Proc. Natl. Acad. Sci. U.S.A. 99 (26):16899-16903 (2002).
Cooper, N. et al., "Synthesis of novel PBDs as anti-tumour agents," Chem. Commun. (2002) 16:1764-1765.
Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.
Corey et al., "LuCap35: a new model of prostate cancer progression to androgen independence." The Prostate 2003;55:239-46.
Courtney, S. M. et al., "A new convenient procedure for the synthesis of pyrrolo[2,1-c][1,4]benzodiazepines", Tetrahedron Letters, vol. 34, No. 33, 5327-28 (1993).
Coussens L., et al., "Tyrosine Kinase Receptor with Extensive Homology to EGF Receptor Shares Chromosomal Location With neu Oncogene," Science (1985) 230(4730):1132-1139.
Cragg et al., "The alternative transcript of CD79b is overexpressed in B-CLL and inhibits signaling for apoptosis," Blood (2002) 100 (9):3068-3076.
Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.
Crouch et al., "The use• of ATP bioluminescence as a measure of cell proliferation and cytotoxicity," (1993) J. Immunol. Meth. 160:81-88.
Dall'Acqua, W. F. et al., "Antibody humanization by framework shuffling" Methods, 36, 43-60 (2005).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Davis et al., "Identification of a family of Fe receptor homo logs with preferential B cell expression," (2001) Proc. Natl. Acad. Sci. USA 98(17):9772-9777.
De Groot et al., "Cascade-Release Dendrimers Liberate All End Groups upon a Single Triggering Event in the Dendritic Core," (2003) Angew. Chem. Int. Ed. 42:4490-4494.
De Groot et al., "Elongated Multiple Electronic Cascade and Cyclization Spacer Systems in Activatible Anticancer Prodrug for Enhanced Drug Release," (2001) J. Org. Chem. 66:8815-8830.
De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.

Dennis et al., (2002) "Albumin Binding as a General Strategy for Improving The Pharmacokinetics of Proteins" J Biol Cherm. 277:35035-35043.
Dijke, P., et al., "Characterization of Type I Receptors for Transforming Growth Factor-beta and Activin," Science 264 (5155):101-104 (1994).
Dimasi et al., "Efficient preparation of site specific antibody drug conjugates using cysteine insertion," Mol. Pharmaceutics 14 1501-1516 (2017).
Dimasi et al., "The Design and Characterization of Oligospecific Antibodies for Simultaneous Targeting of Multiple Disease Mediators" Journal of Molecular Biology, 2009, 393, 672-692.
Dobner et al., "Differentiation-specific expression of a novel G protein-coupled receptor from Burkitt's lymphoma," (1992) Eur. J. Immunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the CRI PTO Autosomal Gene and Its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of *Staphylococcus aureus* to subinhibitory concentrations of a sequence-selective, DNA minor groove crosslinking pyrrolobenzodiazepine dimer," J. Antimicrob. Chemo., Aug. 2009, 64(5):949-959.
Dubowchik et al., "Cathepsin B-sensitive dipeptide prodrugs. 1. A model study of structural requirements for efficient release of doxorubicin." Bioorg Med Chem Lett. Dec. 1, 1998; 8(23):3341-6.
Dubowchik et al., "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation By IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Eliel et al., Stereochemistry of Organic Compounds, John Wiley & Sons, Inc., New York (1994).
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8):4426-4433.
Farmer, J.D. et al., "Synthesis and DNA crosslinking ability of a dimeric anthramycin analog," Tetrahedron Letters (1988) 29(40):5105-5108, Abstract only.

(56) References Cited

OTHER PUBLICATIONS

Farmer, J.D. et al., "DNA binding properties of a new class of linked anthramycin analogs,", Chemical Abstracts, Abstract No. 239940r, vol. 114, No. 25, 25 899-903 (1991).
Fey, T. et al., "Silica-supported TEMPO catalyst: synthesis and application in the anelli oxidation of alcohols," J. Org. Chem. (2001) 66:8154-8159.
Field, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The ephrins and Eph receptors in neural development," Annu. Rev. Neurosci. 21:309-345 (1998).
Flygare, "Antibody-drug conjugates for the treatment of cancer," Chem. Biol. & Drug Design (2013) 81(1):113-121.
Flynn et al., "Pre-Clinical Activity of Adct-301, a Novel Pyrrolobenzodiazepine (PBD) Dimer-Containing Antibody Drug Conjugate (ADC) Targeting CD25-Expressing Hematological Malignancies," https://www.researchgate.net/publication/275520174.
Foloppe, M.P. et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.
Geiser et al. "Automation of solid-phase peptide synthesis" in Macromolecular Sequencing and Synthesis, Alan R. Liss, Inc., 1988, pp. 199-218.
Genbank accession No. 11038674 (2013).
Genbank accession No. 20 NM_006424 (2013).
Genbank accession No. AAH32229, version No. AAH32229.1 GI:21619004, record update: Mar. 6, 2012.
Genbank accession No. AB040878 (2001).
Genbank accession No. AF116456 (1999).
Genbank accession No. AF179274 (2001).
Genbank accession No. AF229053 (2000).
Genbank accession No. AF343662 (2001).
Genbank accession No. AF343663 (2001).
Genbank accession No. AF343664 (2001).
Genbank accession No. AF343665 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession No. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. M76125, version No. M76125.1 GI:292869, 1995.
Genbank accession No. NM_000626 (2013).
Genbank accession No. NM_001178098.1 (2012).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. NP 002111.1 (2013).
Genbank accession No. NP_001171569.1 (1992).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "TENB2, a proteoglycan identified in prostate cancer that is associated with disease progression and androgen independence," (2001) Int J Cancer. Oct. 15; 94(2): 178-184.
Gordon et al., "Somatic hypermutation of the B cell receptor genes B29 (Igβ, CD79b) and mb1 (Igα, CD79a)," PNAS, Apr. 11, 2003, vol. 100, No. 7, 4126-4131.
Greene, T.W. and Wuts, P.G.M., Protective Groups in Organic Synthesis, John Wiley & Sons, 2nd ed., Ch 7, 315-345 (1991).
Greene, T.W. et al., Protective Groups in Organic Synthesis, John Wiley & Sons (1999) 3rd Edition, 503-549.
Greene, T.W. et al., Protective Groups in Organic Synthesis, John Wiley & Sons (1999) 3rd Edition, 23-200.

(56) References Cited

OTHER PUBLICATIONS

Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu, Z. et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41 (12): 1811-1818.
Guiotto, A. et al., "Synthesis of novel C7-aryl substituted pyrrolo[2,1-c][1,4]benzodiazepines (PBDs) via Pro- N10-troc protection and Suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "molecular cloning and expression pattern of a human gene homologous to the murine mb-1 gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Haisma et al., "Comparison of two antracycline-based prodrugs for activation by a monoclonal antibody-β-glucuronidase conjugate in the specific treatment of cancer." Cell biophysics, Humana Press Inc. 1994, 24/25: 185-192.
Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.
Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by *streptomyces* sp.", J. Antibiotics, 41, 702-704 (1988).
Hartley JA: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "Abstract 2856: pyrrolobenzodiazepine (PBD) dimers—potent next generation warheads in antibody drug conjugates (ADCs) targeted at both solid and haematological tumors," Cancer Res. (2013) 78(8)Supp 1:2856.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (lg-alpha/mb-1) gene," (1994) Immunogenetics 40(4 ):287-295.
Hay et al., "A 2-nitroimidazole carbamate prodrug of 5-amin0-1-(chloromethyl)-3-[(5,6,7-trimethoxyindol-2-yl)carbonyl]-1,2-dihydr0-3h-benz[e]indole (amino-seco-cbi-tmi) for use with adept and gdept," (1999) Bioorg. Med. Chem. Lett. 9:2237-2242.
Herdwijn et al., "Synthesis of trans(+ )6-phenoxyacetamido-1-methylene-3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mutation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Surviv Factor for Hippocampal and Mesencephalic Neurons," (2000) Genomics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1- c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1-c][1,4]benzodiazepine monomers,"

(56) References Cited

OTHER PUBLICATIONS

Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the pyrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
International Search Report and Written Opinion dated Dec. 21, 2012 for Int. Appl. No. PCT/US2012/059864 (7 pages).
International Search Report and Written Opinion for Application No. PCT/EP2012/070233 dated Jan. 28, 2013 (8 pages).
International Search Report and Written Opinion for Application No. PCT/EP2013/071346 dated Feb. 5, 2014 (11 pages).
International Search Report and Written Opinion for Application No. PCT/EP2013/071352 dated Feb. 5, 2014 (14 pages).
International Search Report and Written Opinion for Application No. PCT/EP2014/054958 dated Jul. 2, 2014 (13 pages).
International Search Report and Written Opinion for Application No. PCT/GB2015/052629 dated Nov. 2, 2015 (12 pages).
International Search Report and Written Opinion for Application No. PCT/US2011/032664 dated Aug. 19, 2011 (13 pages).
International Search Report and Written Opinion for Application No. PCT/US2011/032668 dated May 26, 2011 (12 pages).
International Search Report and Written Opinion for Application No. PCT/US2015/050634 dated Jan. 29, 2016 (14 pages).
International Search Report and Written Opinion for Application No. PCT/EP2018/053163 dated Apr. 4, 2018, 10 pages.
International Search Report and Written Opinion for Application No. PCT/EP2018/053162 dated Apr. 24, 2018 (9 pages).
International Search Report and Written Opinion for Application No. PCT/EP2018/081079 dated Feb. 19, 2019 (12 pages).
International Search Report and Written Opinion dated Jun. 13, 2019, Int. Appl. No. PCT/EP2019/055116, 6 pages.
Iontcho R Vlahov et al., "Preparation of pyrrolobenzodiazepine peptide conjugates for treating cancer diseases." WO2017172930, Oct. 5, 2017 pp. 1-6.
Itoh et al., "Sibanomicin, a new pyrrolo(1,4)benzodiazepine antitumor antibiotic produced by a *micromonospora* sp." J. Antibiotics, 41, 1281-1284 (1988).
Janjigian, Y.Y., "A phase I trial of SJG-136 (NSC#694501) in advanced solid tumors," Cancer Chemotherapy and Pharmacology, Aug. 2009, 65(5):833-838.
Jeffrey et al., "A Potent Anti-CD70 Antibody-Drug Conjugate Combining a Dimeric Pyrrolobenzodiazepine Drug with Site-Specific Conjugation Technology." Bioconj. Chem. 2013, 24, 1256-1263.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).

Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jones et al., "Releasable Luciferin—Transporter Conjugates: Tools for the Real-Time Analysis of Cellular Uptake and Release," J. Am. Chem. Soc., 2006, 128, 6526-6527.
Jonsson et al., "Human class II DNA and DOB genes display low sequence variability," (1989) Immunogenetics 29(6):411-413.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.
Kamal et a., "Pyrrolo[2,1-c][1,4]benzodiazepine-β-glucuronide prodrugs with a potential for selective therapy of solid tumors by PMT and ADEPT strategies" Bioorganic & Medicinal Chemistry Letters 2008, 18:3769-3773.
Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.
Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.
Kamal, A., "Development of pyrrolo[2,1-c][1,4]benzodiazepine beta-galactoside prodrugs for selective therapy of cancer by ADEPT and PMT," Chemmedchem (2008) 3:794-802.
Kamal, A., "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.
Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.
Kamal, A., "Synthesis of fluorinated analogues of SJG-136 and their DNA-binding potential," Bioorg. Med. Chem. Lett (2004) 14(22):5699-5702.
Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).
Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).
Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.
Kaneko, T. et al., "Bicyclic and tricyclic analogues of anthramycin," J. Med. Chem. (1985) 28:388-392.
Kang, G.-D. et al., "Synthesis of a novel C2-aryl substituted 1 ,2-unsaturated pyrrolobenzodiazepine," Chem. Commun. (2003) 1680-1689.
Kasahara et al., "Nucleotide sequence of a chimpanzee DOB eDNA clone," (1989) Immunogenetics 30(1):66-68.
King et al., "Facile synthesis of maleimide bifunctional Jinkers," (2002) Tetrahedron Letters 43:1987-1990.
Kingsbury et al., "A Novel Peptide Delivery System Involving Peptidase Activated Prodrugs as Antimicrobial Agents. Synthesis and Biological Activity of Peptidyl Derivatives of 5 Fluorouracil," (1984) J. Med. Chem. 27:1447-1451.

(56) References Cited

OTHER PUBLICATIONS

Kitamura et al., "Synthetic study of (+)-anthramycin using ring-closing enyne metathesis and cross-metathesis," Tetrahedron 2004, 60, 9649-9657.
Kohler et al., "Continuous cultures of fused cells secreting antibody of predefined specificity," (1975) Nature 256:495-497.
Kohn, K., "Anthramycin," Antibiotics III, Springer-Verlag, NY, 3-11 (1975).
Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.
Konishi, M. et al., "Chicamycin, a new antitumor antibiotic II. Structure determination of chicamycins A and B," J. Antibiotics, 37, 200-206 (1984).
Kovtun et al., "Antibody-Drug Conjugates Designed to Eradicate Tumors with Homogeneous and Heterogeneous Expression of the Target Antigen," (2006) Cancer Res. 66(6):3214-3121.
Kreitman et al., "Phase I Trial of Recombinant Immunotoxin Anti-Tac(Fv)-PE38 (LMB-2) in Patients with Hematologic Malignancies," J. Clin. Oncol., 2000, 18:1622-1636.
Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.
Kumar et al., "Antibody drug conjugates," Annual Reports in Medicinal Chemistry 2017, 50 441-480.
Kuminoto, et al., "Mazethramycin, a new member of anthramycin group antibiotics" J Antibiot (Tokyo) Jun. 1980; 33(6):665-7.
Kurebayashi et al., "Isolation and characterization of a new human breast cancer cell line, KPL-4, expressing the Erb B family receptors and interleukin•6," (1999) Brit. Jour. Cancer 79(5-6):707-717.
Lambert, "Drug-conjugated monoclonal antibodies for the treatment of cancer," (2005) Current Opin.In Pharmacal. 5:543-549.
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Larhammar et al., "Sequence of Gene and eDNA Encoding Murine Major Histocompatibility Complex Class II Gene AP2*," (1985) J. Biol. Chem. 260(26):14111-14119.
Launay et al., "TRPM4 Is a Ca2+—Activated Nonselective Cation Channel Mediating Cell Membrane Depolarization," Cell 109 (3):397-407 (2002).
Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.
Lazar et al., "A molecular immunology approach to antibody humanization and functional optimization" Molecular Immunology, 2007, 44(8), 1986-1998.
Le et al., "Primary structure and expression of a naturally truncated human P2X ATP receptor subunit from brain and immune system," (1997) FEBS Lett. 418(1-2):195-199.
Leabman; et al., "Effects of altered FcγR binding on antibody pharmacokinetics in cynomolgus monkeys." MAbs. Nov.-Dec. 2013; 5(6):896-903.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Leimgruber, W. et al., "Total synthesis of anthramycin," J. Am. Chem. Soc., 90, 5641-5643 (1968).
Leonard et al., "Phase I/II trial of epratuzumab (humanized anti-CD22 antibody) in indolent non-Hodgkin's lymphoma," J. Clin. Oncology (2003) 21(16):3051-3059.
Leonard et al., "Preclinical and clinical evaluation of epratuzumab (anti-CD22 IgG) in B-cell malignancies," Oncogene (2007) 26:3704-3713.
Leung et al., "Construction and characterization of a humanized, internalizing, B-cell (CD22)-specific, leukemia/lymphoma antibody, LL2," Mol. Immunol. (1995) 32(17-18):1413-1427.
Levenson et al., "MCF-7: The First Hormone-responsive Breast Cancer Cell Line," (1997) Cancer Res. 57(15):3071-3078.
Lewis Phillips et al., "Targeting HER2-Positive Breast Cancer with Trastuzumab-DM1, an Antibody-Cytotoxic Drug Conjugate," Cancer Res, 2008, 68: (22).
Liang et al., "The Gene fora Novel Transmembrane Protein Containing Epidermal Growth Factor and Follistatin Domains is Frequently Hypermethylated in Human Tumor Cells," (2000) Cancer Res. 60:4907-4912.
Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.
Lonberg, "Fully Human antibodies from transgenic mouse and phage display platforms" Curr. Opinion, 20(4), 450-459 (2008).
Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.
Manfre et al., "Syntheses of Proline Analogues as Potential Mechanism-Based Inhibitors of Proline Dehydrogenase:4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.
Marin, D., "Voltammetric studies of the interaction of pyrrolo[2,1-][1,4]benzodiazepine (PBD) monomers and dimers with DNA," J. Electroanal. Chem. (2006) 593(1-2):241-246.
Marks et al., "By-passing Immunization, Human Antibodies from V-gene Libraries Displayed on Phage," (1991) J. Mol. Biol., 222:581-597.
Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.
Masterson et al. "Synthesis and biological evaluation of novel pyrrolo[2,1-c][1,4]benzodiazepine prodrugs for use in antibody-directed enzyme prodrug therapy.", Bioorganic & Medicinal Chemistry Letters, vol. 16., No. 2, Jan. 15, 2006, pp. 252-256.
Mastroberardino et al., "Amino-acid transport by heterodimers of 4F2hc/CD98 and members of a permease family," Nature 395 (6699):288-291 (1998).
Matsumoto, K. et al., "Synthesis of polyaminoalkyl substituted conjugates of pyrrolo[2,1-c][1,4]benzodiazepine (PBD)-polyaminoalkyl involving SNA4 reaction of 2-nitro-5-fluorobenzoate precursors," Heterocycles (2000) 52(3):1015-1020.
McDonagh, "Engineered antibody-drug conjugates with defined sites and stoichiometries of drug attachment," (2006) Protein Eng. Design & Sel. 19(7): 299-307.
Mendoza et al., "Inhibition of Ligand-mediated HER2 Activation in Androgen-independent Prostate Cancer," (2002) Cancer Res. 62:5485-5488.
Miller et al., "Design, Construction, and In Vitro Analyses of Multivalent Antibodies," (2003) Jour. of Immunology 170:4854-4861.
Miller et al., "IRTAs: a new family of immunoglobulinlike receptors differentially expressed in B cells," Blood 99 (8):2662-2669 (2002).
Miura et al., "Molecular cloning of a human RP105 homologue and chromosomal localization of the mouse and human RP105 genes (Ly64 and LY64)." Genomics. Dec. 15, 1996; 38(3):299-304.
Miura et al., "RPIOS is Associated With MD-1 and Transmits an Activation Signal in Human B Cells," (1998) Blood 92:2815-2822.

(56) References Cited

OTHER PUBLICATIONS

Moore M., et al., "Molecular cloning of the eDNA encoding the Epstein-Barr virus/C3d receptor (complement receptor type 2) of human B lymphocytes," Proc. Natl. Acad. Sci. U.S.A. 84, 9194-9198, 1987.
Mori, M. et al., "Total syntheses of prothracarcin and tomaymycin by use of palladium catalyzed carbonylation," Tetrahedron (1986) 42(14):3793-3806.
Morrison et al., "Chimeric human antibody molecules: Mouse antigen-binding domains with human constant region domains," (1984) Proc. Natl. Acad. Sci. USA, 81:6851-6855.
Mountzouris, J.A. et al., "Comparison of a DSB-120 DNA interstrand cross-linked adduct with the corresponding bis-Tomamycin adduct," J. Med. Chem. (1994) 37:3132-3140.
Muller et al., "Cloning and sequencing of the eDNA encoding the human homologue of the murine immunoglobulin-associated protein B29," (1992) Eur. J. Immunol. 22 (6): 1621-1625.
Mungall A.J., et al., "The DNA sequence and analysis of human chromosome 6," Nature 425, 805-811, 2003.
Murphy et al., "Concise, Stereoselective Route to the Four Diastereoisomers of 4-Methylproline." J. Nat. Prod. 2008, 71: 806-809.
Nadler et al., "B4, a human B lymphocyte-associated antigen expressed on normal, mitogen-activated, and malignant B lymphocytes," Journal of Immunology, 1983, 131(1):244-250.
Nagasaka, T. and Koseki, Y, "Stereoselective Synthesis of Tilivalline," Journal of Organic Chemistry, vol. 63, No. 20, 6797-6801 (1998).
Nagasaka, T et al., "Stereoselective Synthesis of Tilivalline," Tetrahedron Letters, 30:14, 1871-1872 (1989).
Nagase T., et al., "Prediction of the Coding Sequences of Unidentified Human Genes. XVII. The Complete Sequences of 100 New eDNA Clones from Brain Which Code for Large Proteins in vitro," (2000) DNA Res. 7 (2):143-150.
Nakamuta M., et al., "Cloning and sequence analysis of a cDNA encoding human non-selective type of endothelin receptor," Biochem. Biophys. Res. Commun. 177, 34-39, 1991.
Nakayama et al., "Altered Gene Expression upon BCR Cross-Linking in Burkitt's Lymphoma B Cell Line," (2000) Biochem. Biophys. Res. Commun. 277(1):124-127.
Narayanaswamy, M., "A novel HPLC/MS assay to measure DNA interstrand cross-linking efficacy in oligonucleotides of varying sequence," EJC Supplements (Nov. 2006) 4(12):92-93.
Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.
Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.
Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.
Naruse et al., "The HLA-DOB gene displays limited polymorphism with only one amino acid substitution," (2002) Tissue Antigens 59:512-519.
Neuberger and Williams, "The intron requirement for immunoglobulin gene expression is dependent upon the promoter," (1988) Nucleic Acids Res. 16:6713-6724.
Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.
Nilius et al., "Voltage Dependence of the Ca2+-activated Cation Channel TRPM4," The Journal of Biological Chemistry, vol. 278, No. 33, Issue of Aug. 15, pp. 30813-30820, 2003.

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).
O'Neil, I.A., et al., "The Synthesis of Functionalized Pyrrolo-[2,1-c][1,4]-Benzodiazepines," Synlett, 75-78 (1997).
Ogawa Y., et al., "Molecular Cloning of a Non-Isopeptide-Selective Human Endothelin Receptor," Biochem. Biophys. Res. Commun. 178, 248-255, 1991.
Okamoto Y., et al. "Palmitoylation of Human Endothelin B," Biol. Chem. 272, 21589-21596, 1997.
O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).
Parrish-Novak J., et al., "Interleukins 19, 20, and 24 Signal through Two Distinct Receptor Complexes," J. Biol. Chem. 277, 47517-47523, 2002.
Paul, Fundamental Immunology, 3rd Edition, pp. 292-295.
Payne, G. "Progress in immunoconjugate cancer therapeutics," (2003) Cancer Cell 3:207-212.
Pei et al., "Exploration of Pyrrolobenzodiazepine (PBD)-Dimers Containing Disulfide-Based Prodrugs as Payloads for Antibody-Drug Conjugates." Mol Pharm. Sep. 4, 2018;15(9):3979-3996.
Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.
Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.
Phillips et al., "Targeting HER2-Positive Breast Cancer with Trastuzumab-DM1, an Antibody-Cytotoxic Drug Conjugate," (2008) Cancer Res. 68(22):9280-9290.
Pingault V., et al., "SOX10 mutations in chronic intestinal pseudo-obstruction suggest a complex physiopathological mechanism," (2002) Hum. Genet. 111, 198-206.
Pletnev S., et al., "Characterization of the Recombinant Extracellular Domains of Human Interleukin-20 Receptors and Their Complexe with Interleukin-19 and Interleukin-20," (2003) Biochemistry 42:12617-12624.
Porkaa et al., "Cloning and Characterization of a Novel Six-Transmembrane Protein STEAP2, Expressed in Normal and Malignant Prostate," Lab. Invest. 82 (11):1573-1582 (2002).
Prasad et al.,"Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Purser, et al., "Fluorine in Medicinal Chemistry." Chem. Soc. Rev., 2008, 37, 320-330.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.

(56) References Cited

OTHER PUBLICATIONS

Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Roguska et al., "A comparison of two murine monoclonal antibodies humanized by CDR-grafting and variable domain resurfacing," Protein Eng, 1996, 9(10):895-904.
Roguska et al., "Humanization of murine monoclonal antibodies through variable domain resurfacing," PNAS, 1994, 91(3):969-973.
Ross et al., "Prostate Stem Cell Antigen as Therapy Target: Tissue Expression and in Vivo Efficacy of an Immunoconjugate," (2002) Cancer Res. 62:2546-2553.
Rudikoff et al., Single amino acid substitution altering antigen-binding specificity. Proc Natl Acad Sci U S A. Mar. 1982; 79(6):1979-83.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "B lymphocyte lineage-restricted expression of mb-1, a gene with CD3-like structural properties," (1988) EMBO J. 7(11):3457-3464.
Sakamoto A, Yanagisawa M., et al., "Cloning and Functional Expression of Human cDNA For the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, The DOBeta Gene Is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J . Am. Chem. Soc. 126:1726-1731.
Sharkey et al., "Epratuzumab-SN-38: a new antibody-drug conjugate for the therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).
Sinha S.K., et al., "Characterization of the EBV/C3d Receptor on the Human Jurkat T Cell Line: Evidence fora Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse eDNA sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody-Multidrug Immunoconjugates," (2002) Bioorganic & Medicinal Chemistry Letters 12:2213-2215.
Sutherland et al., "SGN-CD33A: a novel CD33-targeting antibody-drug conjugate using a pyrrolobenzodiazepine dimer is active in models of drug-resistant AML." Blood 2013, 122:1455-1463.
Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Talpur et al., "CD25 Expression is Correlated with Histological Grade and Response to Denileukin Diftitox in Cutaneous T-Cell Lymphoma," J. Investigative Dermatology, 2006, 126: 575-583.
Tawaragi Y., et al., "Primary Structure of Nonspecific Crossreacting Antigen (NCA), a Member of Carcinoembryonic Antigen (CEA) Gene Family, Deduced From cDNA Sequence," Biochem. Biophys. Res. Commun. 150, 89-96, 1988.

(56) References Cited

OTHER PUBLICATIONS

Tercel, M. et al., "Unsymmetrical DNA cross-linking agents: combination of the CBI and PBD pharmacophores," J. Med. Chem. (2003) 46:2132-2151.
Thompson J.S., et al., "BAFF-R, a Newly Identified TNF Receptor That Specifically Interacts with BAFF," Science 293 (5537), 2108-2111 (2001).
Thurston, D. E., "Advances in the study of Pyrrolo[2,1-c][1,4]benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien et al., "Design and Synthesis of Tesirine, a Clinical Antibody-Drug Conjugate Pyrrolobenzodiazepine Dimer Payload." ACS Med Chem Lett. Nov. 10, 2016; 7(11): 983-987.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al., "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
U.S. Appl. No. 62/547,303, filed Aug. 18, 2017.
Van Geel et al., "Chemoenzymatic Conjugation of Toxic Payloads to the Globally Conserved N-Glycan of Native mAbs Provides Homogeneous and Highly Efficacious Antibody-Drug Conjugates," (2015) Bioconjugate Chem. 26: 2233-2242.
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identifigation of a human protein homologous to the mouse Lyb-2 B cell differentiation antigen and sequence of the corresponding cDNA," (1990) J. Immunol. 144(12):4870-4877.
Wakankar, et al., "Physicochemical stability of the antibody-drug conjugate Trastuzumab-DM1: changes due to modification and conjugation processes." Bioconjugate Chemistry, 2010, 21, 1588-1595.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial cDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for c3d and the epstein-barr virus and relatedness to other members of the family of C3/C4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson "Eph Receptors and Ephrins: Regulators of Guidance and Assembly," Int. Rev. Cytol. 196:177-244 (2000).
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "cDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Wu et al., "Arming antibodies: prospects and challenges for immunoconjugates," (2005) Nature Biotech. 23(9):1137-1145.

(56) References Cited

OTHER PUBLICATIONS

Wuts, P & Greene, T, Greene's Protective Groups in Organic Synthesis, Fourth Edition (Wiley-Interscience), 2007.

Xie et al., "In vivo behaviour of antibody-drug conjugates for the targeted treatment of cancer," (2006) Expert. Opin Biol. Ther. 6(3):281-291.

Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.

Xu et al., "Molecular Cloning, Functional Characterization, Tissue Distribution, and Chromosomal Localization of a Human, Small Intestinal Sodium—Phosphate (Na+—Pi) Transporter (SLC34A2)," Genomics 62 (2):281-284 (1999).

Xu, M.J., et al., "Molecular Cloning and Characterization of SPAP1, an Inhibitory Receptor," (2001) Biochem. Biophys. Res. Commun. 280 (3):768-775.

Xu, X.Z., et al., "Regulation of melastatin, a TRP-related protein, through interaction with a cytoplasmic isoform," Proc. Natl. Acad. Sci. U.S.A. 98 (19):10692-10697 (2001).

Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Younes et al., "Phase I multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776-82.

Yu et al., "Human mb-1 gene: complete edna sequence and its expression in b cells bearing membrane Ig of various isotypes," (1992) J. Immunol. 148(2) 633-637.

Zammarchi et al., "Pre-Clinical Development of Adct-402, a Novel Pyrrolobenzodiazepine (PBD)-Based Antibody Drug Conjugate (ADC) Targeting CD19-Expressing B-Cell Malignancies," Blood, 2015, 126:1564, Abstract.

Zhao et al., "Novel Antibody Therapeutics Targeting Mesothelin in Solid Tumors," (2016) Clin. Cancer Drugs 3: 76-86.

METHODS

CROSS-REFERENCE TO RELATED APPLICATIONS

This application is a national phase application under 35 U.S.C. § 371 of PCT International Application No. PCT/EP2019/0565116, filed Mar. 1, 2019, which claims the benefit of Great Britain Application No. 1803342.3, filed Mar. 1, 2018, each of which are herein incorporated by reference.

The present invention relates to a method of synthesising a compound useful as an intermediate in the synthesis of endo-unsaturated pyrrolobenzodiazepines.

BACKGROUND TO THE INVENTION

Tesirine and related 2,3 unsaturated pyrrolobenzodiazepines are typically made by triflation of a ketone in the C-ring of the system, followed by introduction of radical groups such as methyls, or aryl groups—this approach is described for Tesirine in Tiberghien 2016 and WO 2014/057074:

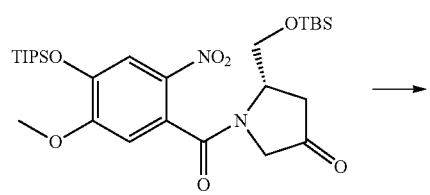

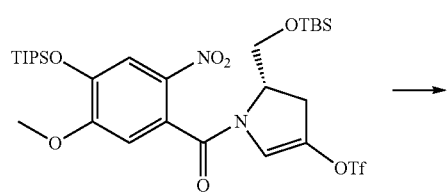

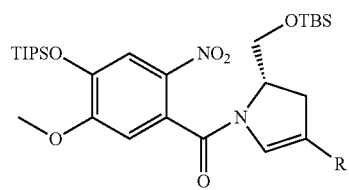

The entire route to Tesirine takes 31 steps, and it is desired to improve the synthesis of Tesirine and related compounds by reducing the number of steps and increasing the overall yield.

DISCLOSURE OF THE INVENTION

The present invention provides an isomerism route to a key endo-unsaturated alkene in the route from a corresponding exo-unsaturated alkene.

A first aspect of the present invention provides a method of synthesising a compound of formula I:

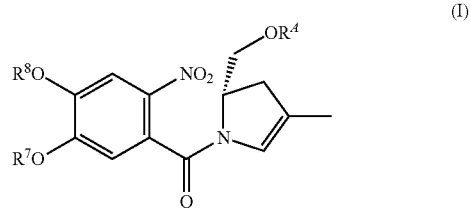

from a compound of formula II:

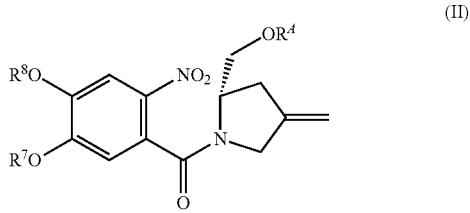

where
$R^A$ is either H or $Prot^{O1}$;
$R^8$ is either:
(i) $Prot^{O3}$; or
(ii) a group of formula A1 in formula (I) and A2 in formula (II):

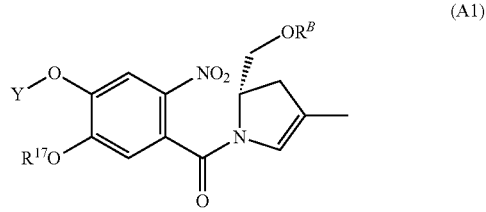

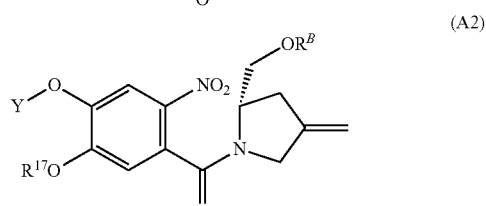

where $R^B$ is either H or $Prot^{O2}$;
$R^7$ is selected from $C_{1-4}$ alkyl and benzyl;
$R^{17}$ is selected from $C_{1-4}$ alkyl and benzyl;
Y is a $C_{3-12}$ alkylene group, which chain may be interrupted by one or more heteroatoms, selected from O, S and $NR^{N2}$ (where $R^{N2}$ is H or $C_{1-4}$ alkyl), or an aromatic ring selected from benzene and pyridine;
$Prot^{O1}$, $Prot^{O2}$ and $Prot^{O3}$ are independently hydroxyl protecting groups which are not labile under the reaction conditions.

The method is carried out using a catalyst, with the optional addition of an additive.

Thus when $R^8$ is $Prot^{O3}$, the reaction is:

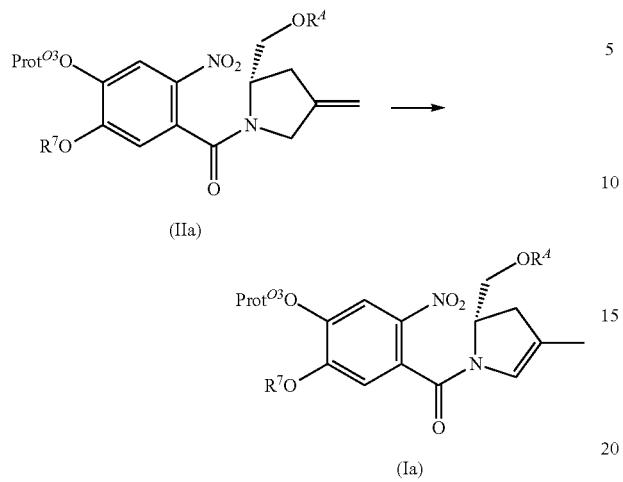

(IIa)

(Ia)

When $R^8$ is a group of formula A1 in formula (I) and A2 in formula (II), the reaction is:

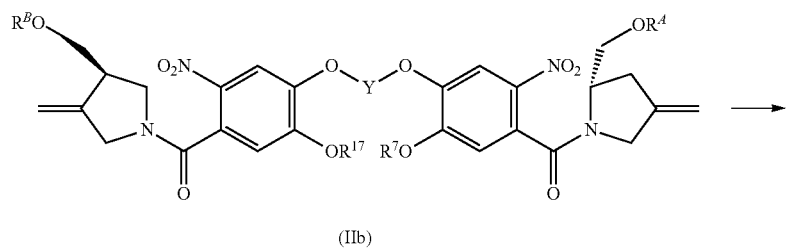

(IIb)

(Ib)

The use of catalysis for isomerism of alkenes is known. For example, a Rh catalyst may be used in the isomerism of an endo double bond in a synthesis of anthramycin (Kitamura 2004):

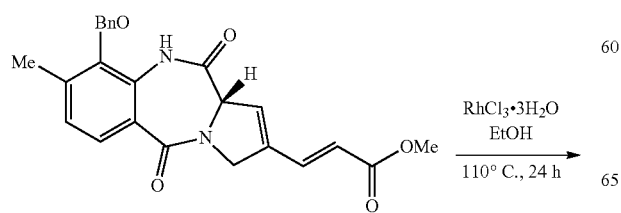

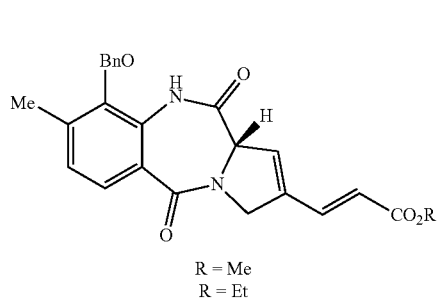

R = Me
R = Et

The present invention avoids the need to use an alkyl Suzuki reaction to generate the compound of formula (I). By doing so, the overall yield may be increased. In addition, the route to compound (I) from commercially available starting materials can be reduced by 2 to 4 steps.

A second aspect of the present invention provides a compound of formula IIa:

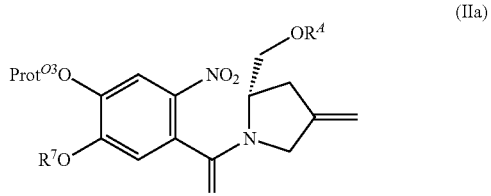

(IIa)

where $R^7$ is selected from $C_{1-4}$ alkyl and benzyl; and
$R^4$ is H or $Prot^{O1}$;

$Prot^{O1}$ and $Prot^{O3}$ are independently hydroxyl protecting groups which are not labile under the reaction conditions of the first aspect of the invention.

Definitions $C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

Benzyl: —$CH_2$-Phenyl.

$C_{3-12}$ alkylene: The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated $C_{3-12}$ alkylene groups include, but are not limited to, —$(CH_2)_n$— where n is an integer from 3 to 12, for example, —$CH_2CH_2CH_2$— (propylene), —$CH_2CH_2CH_2CH_2$— (butylene), —$CH_2CH_2CH_2CH_2CH_2$— (pentylene) and —$CH_2CH_2CH_2CH_2CH_2CH_2CH_2$— (heptylene).

Examples of branched saturated $C_{3-12}$ alkylene groups include, but are not limited to, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{3-12}$ alkylene groups ($C_{3-12}$ alkenylene, and alkynylene groups) include, but are not limited to, —CH=CH—$CH_2$—, —$CH_2$—CH=$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—$CH_2$—CH=CH—, —CH=CH—$CH_2$—$CH_2$—CH=CH—, and —$CH_2$—C≡C—$CH_2$—.

Examples of branched partially unsaturated $C_{3-12}$ alkylene groups ($C_{3-12}$ alkenylene and alkynylene groups) include, but are not limited to, —C($CH_3$)=CH—, —C($CH_3$)=CH—$CH_2$—, —CH=CH—CH($CH_3$)— and —C≡C—CH($CH_3$)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Where the $C_{3-12}$ alkylene group is interrupted by a heteroatom, the subscript refers to the number of atoms in the chain including the heteroatoms. For example, the chain —$C_2H_4$—O—$C_2H_4$— would be a C group.

Where the $C_{3-12}$ alkylene group is interrupted by an aromatic ring, the subscript refers to the number of atoms directly in the chain including the aromatic ring. For example, the chain

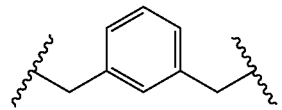

would be a C group.

Hydroxyl protecting group which is not labile under the reaction conditions: Hydroxyl protecting groups are well known in the art, for example, in Wuts & Greene 2007. Those groups suitable for use in the present invention include substituted methyl ethers, substituted ethyl ethers (except those containing unsaturation), methoxy substituted benzyl ethers, silyl ethers and acetates.

Catalyst: Catalysts suitable for use in the present invention are those comprising a metal hydride, or those able to form a metal hydride in situ. These catalysts contain a transition metal, including, but not limited to, Ru, Ir, Rh and Pd.

Additive: The optional additive may be selected from:
(a) a compound suitable to generate a metal hydride in situ in combination with the catalyst;
(b) a base;
(c) an additional ligand for the catalyst.

Further Preferences $R^A$

In some embodiments, $R^A$ is $Prot^{O1}$.
In other embodiments, $R^A$ is H.

$R^B$

In some embodiments, $R^B$ is $Prot^{O2}$.
In other embodiments, $R^B$ is H.

$R^A$ & $R^B$

In some embodiments, $R^A$ is $Prot^{O1}$ and $R^B$ is $Prot^{O2}$.
In other embodiments, $R^A$ is H and $R^B$ is H.

$R^7$

In some embodiments, $R^7$ is a $C_{1-4}$ alkyl group. In some of these embodiments, $R^7$ is methyl. In others of these embodiments, $R^7$ is ethyl.

In some embodiments, $R^7$ is benzyl.

$R^8$

In some embodiments, $R^8$ is $Prot^{O3}$.
In other embodiments, $R^8$ is a group of formula A1 in formula (I) and A2 in formula (II).

$R^{17}$

In some embodiments, $R^{17}$ is a $C_{1-4}$ alkyl group. In some of these embodiments, $R^{17}$ is methyl. In others of these embodiments, $R^{17}$ is ethyl.

In some embodiments, $R^{17}$ is benzyl.

Y

In some embodiment, Y is a $C_{3-12}$ alkylene group which is not interrupted. In some of these embodiments Y is —$(CH_2)_n$— where n is an integer from 3 to 12. In particular, Y may be selected from —$(CH_2)_3$— and —$(CH_2)_5$—.

In other embodiment, Y is a $C_{3-12}$ alkylene group which is interrupted by an aromatic ring.

In some of these embodiments, Y is:

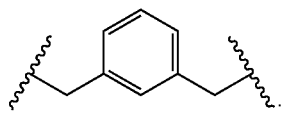 [SMILES: *Cc1cccc(C*)c1]

Hydroxyl Protecting Groups

In some embodiments, $Prot^{O3}$ is orthogonal to $Prot^{O1}$.

In some embodiments, $Prot^{O2}$ and $Prot^{O1}$ are the same.

$Prot^{O1}$ may be selected from substituted methyl ethers, substituted ethyl ethers (except those containing unsaturation), methoxy substituted benzyl ethers, silyl ethers and acetates.

Suitable substituted methyl ethers include, but are not limited to, methoxymethyl (MOM), β-methoxyethoxymethyl ether (MEM), benzyloxymethyl, t-butoxymethyl and siloxymethyl.

Suitable substituted ethyl ethers (except those containing unsaturation), include, but are not limited to, 1-ethoxyethyl, 2-hydroxyethyl, 1-[2-(trimethylsilyl)ethoxy]ethyl, 2,2,2-trichloroethyl, 2-trimethylsilylethyl and t-butyl.

Suitable methoxy substituted benzyl ethers, include, but are not limited to, p-methoxy-benzyl, dimethoxybenzyl and nitrobenzyl.

Suitable silyl ethers include, but are not limited to, trimethylsilyl (TMS), triethylsilyl (TES), tert-butyldimethylsilyl (TBS), tert-butyldiphenylsilyl (TBDPS) and triisopropylsilyl ether (TIPS).

Suitable acetates include, but are not limited to, chloroacetate, methoxyacetate, phenoxyacetate and benzoate.

In some embodiments, $Prot^{O1}$ is a silyl ether, and in particular TBS.

$Prot^{O2}$ may be selected from substituted methyl ethers, substituted ethyl ethers (except those containing unsaturation), methoxy substituted benzyl ethers, silyl ethers and acetates.

Suitable substituted methyl ethers include, but are not limited to, methoxymethyl (MOM), β-methoxyethoxymethyl ether (MEM), benzyloxymethyl, t-butoxymethyl and siloxymethyl.

Suitable substituted ethyl ethers (except those containing unsaturation), include, but are not limited to, 1-ethoxyethyl, 2-hydroxyethyl, 1-[2-(trimethylsilyl)ethoxy]ethyl, 2,2,2-trichloroethyl, 2-trimethylsilylethyl and t-butyl.

Suitable methoxy substituted benzyl ethers, include, but are not limited to, p-methoxy-benzyl, dimethoxybenzyl and nitrobenzyl.

Suitable silyl ethers include, but are not limited to, trimethylsilyl (TMS), triethylsilyl (TES), tert-butyldimethylsilyl (TBS), tert-butyldiphenylsilyl (TBDPS) and triisopropylsilyl ether (TIPS).

Suitable acetates include, but are not limited to, chloroacetate, methoxyacetate, phenoxyacetate and benzoate.

In some embodiments, $Prot^{O2}$ is a silyl ether, and in particular TBS.

$Prot^{O3}$ may be selected from substituted methyl ethers, substituted ethyl ethers (except those containing unsaturation), methoxy substituted benzyl ethers, silyl ethers and acetates.

Suitable substituted methyl ethers include, but are not limited to, methoxymethyl (MOM), β-methoxyethoxymethyl ether (MEM), benzyloxymethyl, t-butoxymethyl and siloxymethyl.

Suitable substituted ethyl ethers (except those containing unsaturation), include, but are not limited to, 1-ethoxyethyl, 2-hydroxyethyl, 1-[2-(trimethylsilyl)ethoxy]ethyl, 2,2,2-trichloroethyl, 2-trimethylsilylethyl and t-butyl.

Suitable methoxy substituted benzyl ethers, include, but are not limited to, p-methoxy-benzyl, dimethoxybenzyl and nitrobenzyl.

Suitable silyl ethers include, but are not limited to, trimethylsilyl (TMS), triethylsilyl (TES), tert-butyldimethylsilyl (TBS), tert-butyldiphenylsilyl (TBDPS) and triisopropylsilyl ether (TIPS).

Suitable acetates include, but are not limited to, chloroacetate, methoxyacetate, phenoxyacetate and benzoate.

In some embodiments, $Prot^{O3}$ is a silyl ether, and in particular TIPS.

Catalysts

Catalysts suitable for use in the present invention are those containing a metal hydride, or those able to form a metal hydride in situ. These catalysts contain a transition metal, including, but not limited to, Ru, Ir, Rh and Pd. In some embodiments, the transition metal is Pd. In other embodiments, the transition metal is Ru. In other embodiments, the transition metal is Rh. In other embodiments, the transition metal is Ir.

In some embodiments, the catalyst comprises P-ligands, such as, but not limited to, $(t-Butyl)_3P$ and $Ph_3P$.

In some embodiments, the catalyst is one which is able to form an active species comprising $PdH(PR^P_3)X$, where each $R^P$ is independently selected from t-butyl and phenyl, and X is halo (e.g. I, Br, Cl).

Particular catalysts of interest include, but are not limited to, the following:

Grubbs I:
Benzylidene-bis(tricyclohexylphosphine)dichlororuthenium,
Bis(tricyclohexylphosphine)benzylidine ruthenium(IV) dichloride,
Dichloro(benzylidene)bis(tricyclohexylphosphine)ruthenium(II)

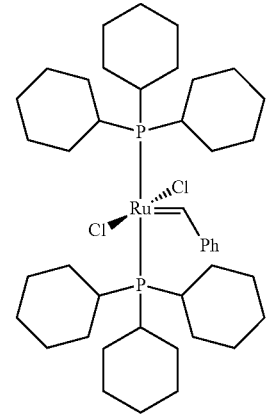

Grubbs II:
(1,3-Bis(2,4,6-trimethylphenyl)-2-imidazolidinylidene)dichloro(phenylmethylene)(tricyclohexylphosphine)ruthenium,
Benzylidene[1,3-bis(2,4,6-trimethylphenyl)-2-imidazolidinylidene]dichloro(tricyclohexylphosphine)ruthenium,
Dichloro[1,3-bis(2,4,6-trimethylphenyl)-2-imidazolidinylidene](benzylidene)(tricyclohexylphosphine)ruthenium(II)

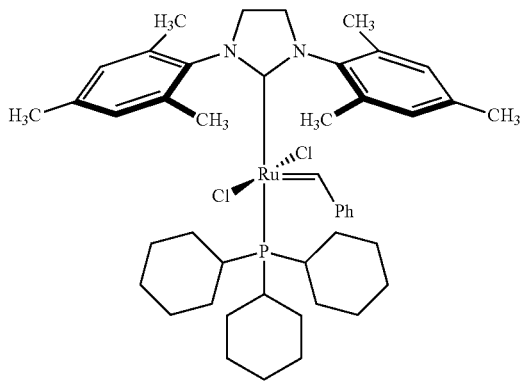

Crabtrees Catalyst:
(1,5-Cyclooctadiene)(pyridine)(tricyclohexylphosphine)-Ir(I) PF$_6$, Iridium(I)hexafluorophosphate (1,5-Cyclooctadiene)-(pyridine)-(tricyclohexylphosphine) complex, [Ir(cod)(PCy$_3$)(py)]PF$_6$

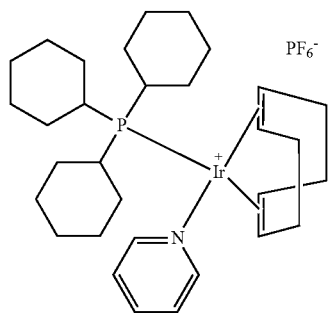

RuHCl(CO)PPh$_3$

Ru-42

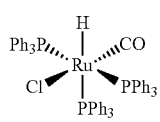

RhH(CO)PPh$_3$

Rh-42
Carbonyltris(triphenylphosphine)rhodium(I)hydride,
Hydridocarbonyl-tris(triphenylphosphine)-rhodium(I),
Rhodium monocarbonyl hydrogen tris(triphenylphosphine),
Rhodium(I) tris(triphenylphosphine) carbonyl hydride,
Tris(triphenylphosphine)carbonylrhodium hydride,
trans-Carbonyl(hydrido)tris(triphenylphosphine)rhodium

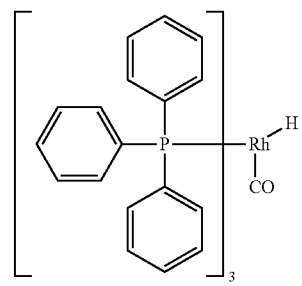

Rh(COD)$_2$BF$_4$

Rhodium(I) tetrafluoroborate 1,5-Cyclooctadiene complex

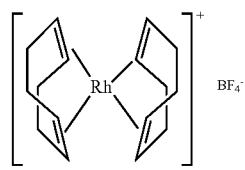

Pd-113:
di-μ-bromobis(tri-tert-butylphosphine)dipalladium(I)
{Pd(μ-Br) [P(tBu)$_3$]}$_2$

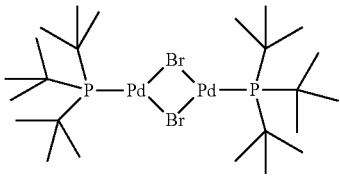

Pd-118:
Pd(dtbpf)Cl$_2$
Dichloro[1,1'-bis(di-tertbutylphosphino)ferrocene]palladium(II)

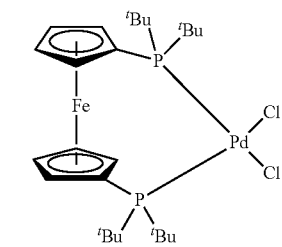

Cationic CpRu(Pr$_3$)
Acetonitrile(cyclopentadienyl)[2-(di-i-propylphosphino)-4-(t-butyl)-1-methyl-1H-imidazole]ruthenium(II) hexafluorophosphate

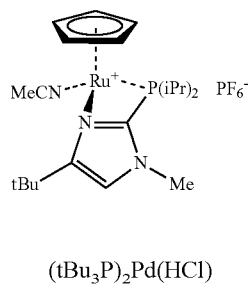
(tBu₃P)₂Pd(HCl)
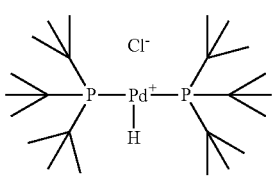
Catalysts of interest may also be generated in situ by the reaction of a metal source and appropriate ligands. The metal sources and ligands of interest include, but are not limited to, the following:
| Metal Sources | |
|---|---|
| Pd(OAc)₂ | |
| Pd(dba)₂ | |
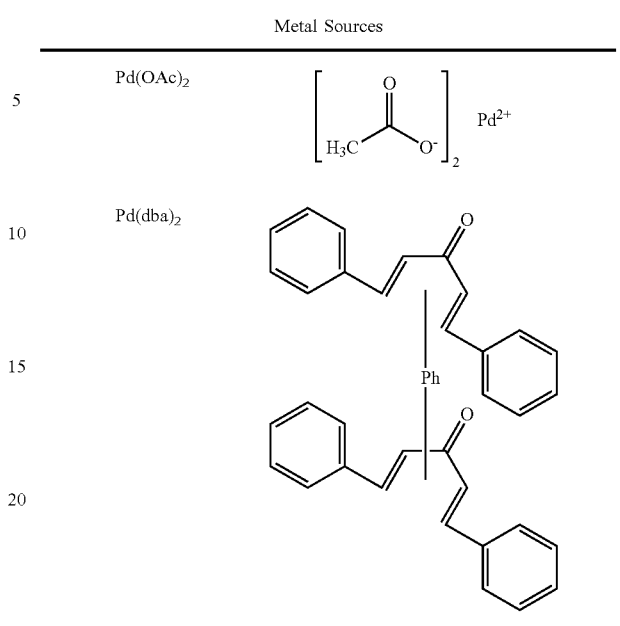
| Ligands | |
|---|---|
| P(OH)(t-Bu)₂ | |
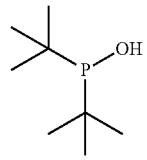
P(t-Bu)₃•HBF₄
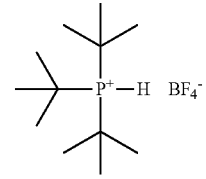
PCy₃•HBF₄
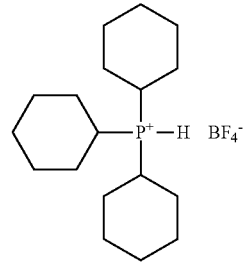
P(t-Bu)₂(Me)•HBF₄
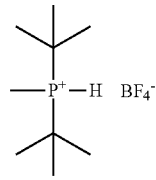

-continued
| Ligands |  |
|---|---|
| P(O-(2,4-t-Bu)-Ph)₃ | 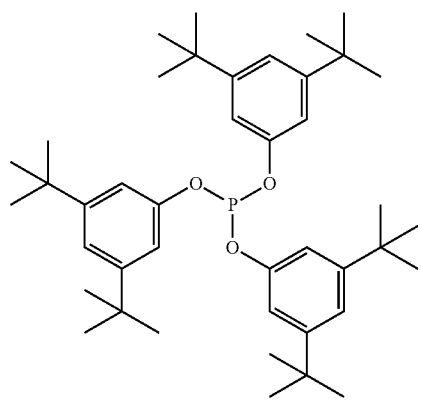 [SMILES: CC(C)(C)c1cc(OP(Oc2cc(C(C)(C)C)cc(C(C)(C)C)c2)Oc2cc(C(C)(C)C)cc(C(C)(C)C)c2)cc(C(C)(C)C)c1] |
| Xantphos | 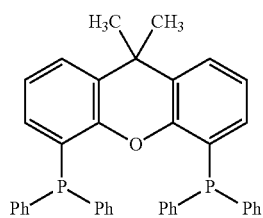 [SMILES: CC1(C)c2cccc(P(c3ccccc3)c3ccccc3)c2Oc2c(P(c3ccccc3)c3ccccc3)cccc21] |
| Phanephos | 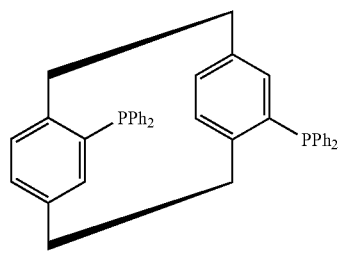 |
| Ru-phos | 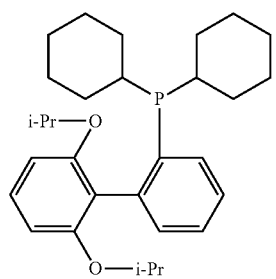 [SMILES: CC(C)Oc1cccc(OC(C)C)c1-c1ccccc1P(C1CCCCC1)C1CCCCC1] |
| P(o-tol)₃ | 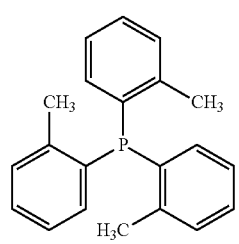 [SMILES: Cc1ccccc1P(c1ccccc1C)c1ccccc1C] |

| Ligands |
| --- |

Biphephos

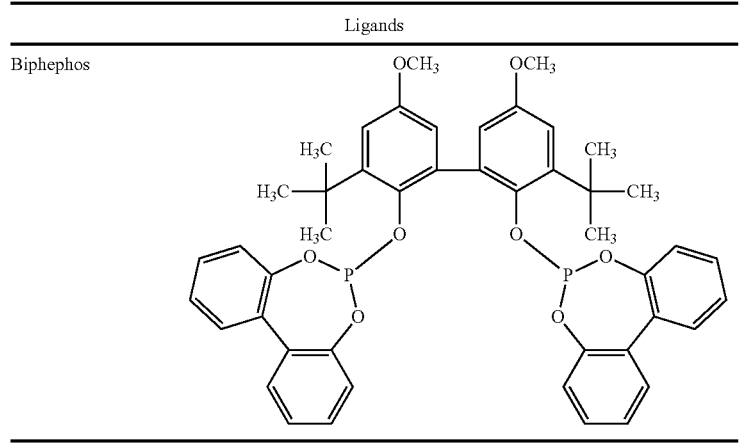

In some embodiments, the catalyst is selected from Pd-113 and ((tBu)$_3$P)$_2$Pd(HCl). In some of these embodiments, the catalyst is Pd-113.

Additives: The optional additive may be selected from:
(a) a compound suitable to generate a metal hydride in situ in combination with the catalyst;
(b) a base;
(c) an additional ligand for the catalyst.

Compounds suitable to generate a metal hydride in situ in combination with the catalyst include, but are not limited to: Et$_3$SiH, iPrCOCl and n-BuOH.

Bases suitable for use in the present invention include, but are not limited to, Et$_3$N.

Additional ligands for the catalyst include, but are not limited to, PPh$_3$ and P(t-Bu)$_3$.

Reaction Conditions

The reaction may be carried out in any suitable solvent, bearing in mind the reaction temperatures employed. It may be preferred that the solvent is not an alcohol. In some embodiments, the solvent is toluene.

The reaction may be carried out at a suitable temperature. In some embodiments, the reaction temperature may be between 5 and 120° C. The minimum temperature may be 5, 10, 15, 20, 30, 40, 50 or 60° C. The maximum temperature may be 120, 110, 100, 90, 80 or 75° C. In some embodiment, the reaction may be carried out at 70° C.

The reaction may be carried out for the amount of time to achieve the desired conversion. In some embodiments, the reaction time may be between half an hour and 48 hours. The minimum time may be 30 minutes, 1 hour, 2 hours, 4 hours or 8 hours. The maximum reaction time may be 48, 36, 24 or 22 hours. In some embodiments, the reaction time may be 2 to 22 hours.

The catalyst may be added in a relative amount to the starting compound of formula (II) of 1 mol % to 30 mol %. The minimum relative amount may be 1, 1.25, 1.5, 2, 2.5 or 5 mol %. The maximum relative amount may be 30, 25, 20, 15 or 10 mol %.

The reaction may be carried out under suitable atmospheric conditions, bearing in mind the desired product. It may be preferred that the atmosphere does not comprise predominantly of hydrogen. In some embodiments, the reaction may be carried out under a substantially inert atmosphere. The atmosphere may be comprised predominantly of nitrogen or may be comprised predominantly of argon. The maximum amount of oxygen in the atmosphere may be 100,000, 50,000, 10,000, 1,000, 100 or 10 ppm. The maximum amount of water in the atmosphere may be 10,000, 1,000, 100, 10 or 1 ppm.

In some embodiments of the first aspect of the present invention, there is provided a method of synthesising a compound of formula I:

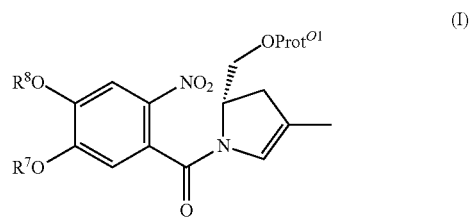

(I)

from a compound of formula II:

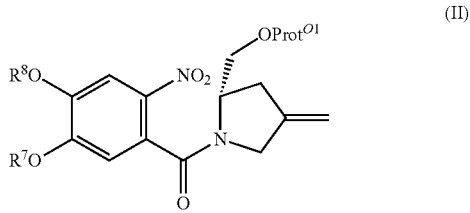

(II)

where R$^8$ is either:
(i) Prot$^{O3}$; or
(ii) a group of formula A1 in formula (I) and A2 in formula (II):

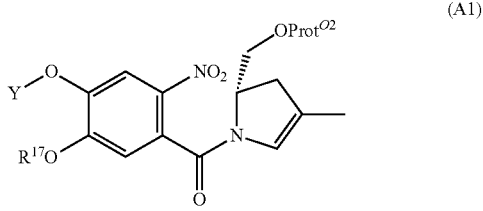

(A1)

-continued (A2)

R[7] is selected from $C_{1-4}$ alkyl and benzyl;
R[17] is selected from $C_{1-4}$ alkyl and benzyl;
Y is a $C_{3-12}$ alkylene group, which chain may be interrupted by one or more heteroatoms, selected from O, S and $NR^{N2}$ (where $R^{N2}$ is H or $C_{1-4}$ alkyl), or an aromatic ring selected from benzene and pyridine;
$Prot^{O1}$, $Prot^{O2}$ and $Prot^{O3}$ are independently hydroxyl protecting groups which are not labile under the reaction conditions.

In some embodiments of the second aspect of the present invention, there is provided a compound of formula IIa:

(IIa)

where R[7] is selected from $C_{1-4}$ alkyl and benzyl;
$Prot^{O1}$ and $Prot^{O3}$ are independently hydroxyl protecting groups which are not labile under the reaction conditions of the first aspect of the invention.

EXAMPLES

The following examples are provided solely to illustrate the present invention and are not intended to limit the scope of the invention, as described herein.
Acronyms
DMF—Dimethylformamide
THF—Tetrahydrofuran
EtOAc—ethylacetate
Boc$_2$O—Di-tert-butyl dicarbonate
TBAF—Tetra-n-butylammonium fluoride
HOBt—Hydroxybenzotriazole
DIC—N,N'-Diisopropylcarbodiimide
rt—room temperature
Vols—1 g of material in 1 ml is 1 volume
General Information Flash chromatography was performed using a Biotage Isolera 1™ using gradient elution with hexane/EtOAc or CH$_2$Cl$_2$/MeOH mixtures as indicated until all UV active components eluted from the column. The gradient was manually held whenever substantial elution of UV active material was observed. Fractions were checked for purity using thin-layer chromatography (TLC) using Merck Kieselgel 60 F254 silica gel, with fluorescent indicator on aluminium plates. Visualisation of TLC was achieved with UV light or iodine vapour unless otherwise stated. Extraction and chromatography solvents were bought and used without further purification from VWR U.K. All fine chemicals were purchased from Sigma-Aldrich or VWR.

The analytical LC/MS conditions (for reaction monitoring and purity determination) were as follows: Positive mode electrospray mass spectrometry was performed using a Shimadzu Nexera®/Prominence® LCMS-2020. Mobile phases used were solvent A (H$_2$O with 0.1% formic acid) and solvent B (CH$_3$CN with 0.1% formic acid).

LCMS-A: Gradient for 3-minute run: Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes at a flow rate of 0.8 mL/min. Column: Waters Acquity UPLC® BEH Shield RP18 1.7 μm 2.1×50 mm at 50° C. fitted with Waters Acquity UPLCO® BEH Shield RP18 VanGuard Pre-column, 130A, 1.7 μm, 2.1 mm×5 mm.

LCMS-B: Gradient for 15-minute run: Initial composition 5% B held over 1 minute, then increased from 5% B to 100% B over a 9 minute period. The composition was held for 2 minutes at 100% B, then returned to 5% B in 10 seconds and held there for 2 minutes 50 seconds. The total duration of the gradient run was 15.0 minutes at a flow rate of 0.6 mL/minute. Detection was monitored at 254 nm, 223 nm and 214 nm. ACE Excel 2 C18-AR, 2μ, 3.0×100 mm fitted with Waters Acquity UPLC® BEH Shield RP18 VanGuard Pre-column, 130A, 1.7 μm, 2.1 mm×5 mm.

Synthesis of Starting Material (i) Methyl (S)-1-(5-methoxy-2-nitro-4-((triisopropylsilyl)oxy)benzoyl)-4-methylenepyrrolidine-2-carboxylate (3)

A round-bottomed flask was charged with a magnetic stirrer, THF (15 mL), 1 (1.89 g, 5.118 mmol, 1.0 eq.), HOBt (761 mg, 5.630 mmol, 1.1 eq.), DIC (872 μL, 5.630 mmol, 1.1 eq.) and i-Pr$_2$NEt (1.96 mL, 11.26 mmol, 2.2 eq.) and the mixture was stirred for 10 min. 2 (1.00 g, 5.630 mmol, 1.1 eq.) was added portionwise and the reaction mixture was stirred for 1 h. The reaction was diluted with CH$_2$Cl$_2$, washed with 0.2N HCl solution, the organics dried over MgSO$_4$ and concentrated in vacuo. Flash column chromatography (20-30% EtOAc in hexane) afforded the desired product as a yellow oil (1.19 g, 47%). LCMS-A: 2.00 min (ES+) m/z 493 [M+H]$^+$, 515 [M+Na]$^+$ (ii) (S)-(2-(hydroxymethyl)-4-methylenepyrrolidin-1-yl)(5-methoxy-2-nitro-4-((triisopropylsilyl)oxy)phenyl)methanone (4)

A round-bottomed flask was charged with a magnetic stirrer, THF (15 mL), 3 (1.17 g, 2.383 mmol, 1.0 eq.) and the stirring mixture was cooled to 0° C. Cautiously, LiBH$_4$ (156 mg, 7.149 mmol, 3.0 eq.) was added and the mixture was stirred for 1 h at 0° C. and a further 1.5 h at rt. The reaction was quenched by the addition of ice cold H$_2$O and the pH adjusted to ca. 6 with 1N HCl. The aqueous mixture was extracted with CH$_2$C$_2$, the organics combined, dried over MgSO$_4$ and concentrated in vacuo to afford the desired product as a yellow foam (1.06 g, 96%) which was used without further purification. LCMS-A: 1.92 min (ES+) m/z 465 [M+H]$^+$, 487 [M+Na]$^+$ (iii) (S)-(2-(((tert-butyldimethylsilyl)oxy)methyl)-4-methylenepyrrolidin-1-yl)(5-methoxy-2-nitro-4-((triisopropylsilyl)oxy)phenyl)methanone (5)

A round-bottomed flask was charged with a magnetic stirrer, CH$_2$Cl$_2$ (10 mL), 4 (1.06 g, 2.281 mmol, 1.0 eq.), imidazole (467 mg, 6.858 mmol, 3.0 eq.) TBSCl (517 mg, 3.429 mmol, 1.5 eq.) and stirred for 1 h, whereupon LCMS indicated the reaction was complete. The reaction mixture was filtered, the filtrate washed with H$_2$O, brine, dried over MgSO$_4$ and concentrated in vacuo. Flash column chromatography (20-30% EtOAc in hexane) afforded the desired product as a yellow oil (1.27 g, 96%). LCMS-A: 2.30 min (ES+) m/z 579 [M+H]$^+$, 601 [M+Na]$^+$ Example 1

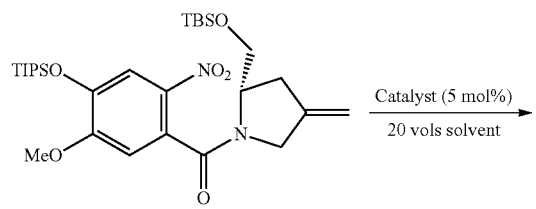 Catalyst (5 mol%) / 20 vols solvent

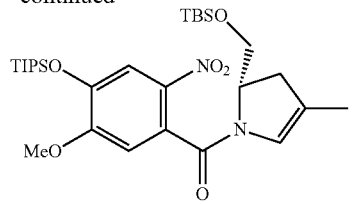

On a 100 mg scale of alkene, reactions were performed in 4 mL vials in a 24-well plate format, situated in an inerted glovebox (<10 ppm O$_2$ and <1 ppm H$_2$O). Metal sources were weighed by hand (if air insensitive) or were dispensed as solids using a Quantos weighing robot situated inside the glovebox. Stir discs were added to each vial.

Starting material (2 g) was dissolved in dry degassed toluene (10 mL total) and 500 μL was dispensed to each vial. (100 mg/reaction). Each vial was then made up to 2 mL with the solvent stated in the reaction plan below. Liquid additives (reactions 2 and 5) were then added. The reactions were sealed and heated at the 60° C. for 4 hours then at 100° C. for a further 18 hours for all reactions except reaction 4 (in MeOH, kept at 60° C.). Samples for uPLC/MS analysis were prepared after 22 hours.

HPLC Conditions/Sampling

λ=220 nm (A1) TEA (0.03 v/v %) in H$_2$O and (B1) TFA (0.03 v/v %) in CH$_3$CN

Column: Phenomenex Kinetex 2.6μ C18 100 Å 75 mm×3 mm Column.

| Time (min) | Flow (mL/min) | % A | % B |
| --- | --- | --- | --- |
| Initial | 1.200 | 30.0 | 70.0 |
| 8.00 | 1.200 | 15.0 | 85.0 |
| 8.50 | 1.200 | 5.0 | 95.0 |
| 8.52 | 1.200 | 30.0 | 70.0 |
| 9.50 | 1.200 | 30.0 | 70.0 |

Run on G64 uPLC. (PC_306)

Sampling: Samples 15 μl-reaction mixture diluted into 1.0 mL MeCN:water (4:1), 0.5 L injection volume.

The conversion amount was calculated as follows:

$$\text{Conversion (\%)} = \frac{100 * (\text{Product Area\%} + \text{Isomeric product Area \%})}{(SM \text{ Area \%}) + (\text{Product Area\%}) + (\text{Isomeric product Area \%})}$$

| Reaction Number | Catalyst | Catalyst (mol %) | Additive | Additive eq. | Temp. ° C. | Solvent (20vols) |
| --- | --- | --- | --- | --- | --- | --- |
| 1 | Grubbs I | 5 | none | | 60-100 | Toluene |
| 2 | Grubbs I | 5 | Et$_3$SiH | 1 | 60-100 | Toluene |
| 3 | Grubbs II | 5 | none | | 60-100 | Toluene |
| 4 | Grubbs II | 5 | none | | 60 | MeOH |
| 5* | none | — | Fe(CO)$_5$ | 3 | 60-100 | CPME |
| 6 | Crabtrees Cat. | 5 | none | | 60-100 | Toluene |
| 7 | Crabtrees Cat. | 5 | none | | 60-100 | IPA/Toluene |
| 8 | RuHCl(CO)PPh$_3$ | 5 | none | | 60-100 | Toluene |
| 9 | cationic CpRu(Pr$_3$) | 5 | none | | 60-100 | Toluene |
| 10 | RhH(CO)PPh$_3$ | 5 | none | | 60-100 | Toluene |
| 11 | Rh(COD)$_2$BF$_4$ | 5 | Binap | 0.05 | 60-100 | Toluene |

-continued

| Reaction Number | Catalyst | Catalyst (mol %) | Additive | Additive eq. | Temp. °C. | Solvent (20vols) |
|---|---|---|---|---|---|---|
| 12 | Pd-113 | 5 | none | | 60-100 | Toluene |
| 13 | Pd-118 | 5 | $Et_3SiH$ | 0.1 | 60-100 | Toluene |

*comparative example

Results

| Reaction Number | Conversion (%) | Product/Isomer ratio | Desired Product (Area %) | Isomeric product (Area %) | Starting Material (Area %) | Other peaks (Area %) |
|---|---|---|---|---|---|---|
| 1 | 20.6 | 0.6 | 7.7 | 12.4 | 77.9 | 2.0 |
| 2 | 32.1 | 1.1 | 12.3 | 11.0 | 49.1 | 27.7 |
| 3 | 19.5 | 5.3 | 14.5 | 2.7 | 71.1 | 11.7 |
| 4 | 100.0 | 0.9 | 46.2 | 52.4 | 0.0 | 1.4 |
| 5 | 0.0 | 0.0 | 0.0 | 0.0 | 70.1 | 29.9 |
| 6 | 13.8 | 22.1 | 12.1 | 0.5 | 78.8 | 8.6 |
| 7 | 100.0 | 0.8 | 29.2 | 36.9 | 0.0 | 33.9 |
| 8 | 100.0 | 0.4 | 26.4 | 68.6 | 0.0 | 5.0 |
| 9 | 100.0 | 0.4 | 25.2 | 71.4 | 0.0 | 3.3 |
| 10 | 47.2 | 0.2 | 6.3 | 38.6 | 50.3 | 4.8 |
| 11 | 100.0 | 0.4 | 25.1 | 56.6 | 0.0 | 18.3 |
| 12 | 100.0 | 15.7 | 89.5 | 5.7 | 0.0 | 4.8 |
| 13 | 100 | 0.3 | 20.5 | 64.4 | 0.0 | 15.2 |

Example 2

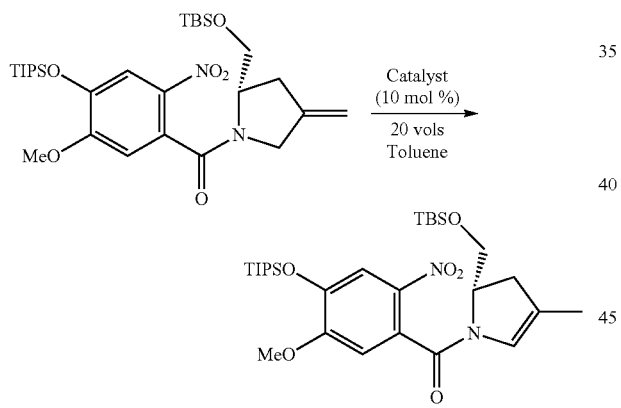

Reactions were performed in 1 mL vials in a 96-well plate format, situated in an inerted glovebox (<10 ppm $O_2$ and <1 ppm $H_2O$). Ligands (12 mol % for bidentate and 20 mol % for monodentate) and Pd-113 were preweighed as solid via Quantos weighing robot inside an inerted glovebox.

Pd sources (10 mol %), IS (4-4'-Di-tert-butyl biphenyl, 10 mol %) were dispensed as 0.01M stock solutions ($CHCl_3$) in the 96-well vials. The carrier solvents were evaporated using a Genevac EZ-2 situated inside a glovebox. Stir discs were added to each vial. Solutions of Alkene starting material (998 mg in 20 mL toluene) were prepared, either alone or with $Et_3SiH$ (27.7 μL) to give 100 mol % alkene and 10 mol % $Et_3SiH$ or with iPrCOCl (18.3 μL) to give 100 mol % alkene and 10 mol % iPrCOCl. 579 μL of each solution was added in each vial to provide 28.9 mg of alkene per reaction. $Et_3N$ (1.4 μL, 20 mol %) was added to each vial that contained a ligand as its $HBF_4$ salt. The reactions were sealed and heated at 80° C. for 20 hours. Samples for uPLC/MS analysis were prepared (as below) at the end of the reaction.

HPLC Conditions/Sampling $\lambda$=220 nm (A1) TFA (0.03 v/v %) in $H_2O$ and (B1) TFA (0.3 v/v %) in $CH_3CN$ Column: Phenomenex Kinetex 2.6μ 18 100 Å 75 mm 3 mm Column.

| Time (min) | Flow (mL/min) | % A | % B |
|---|---|---|---|
| Initial | 1.200 | 30.0 | 70.0 |
| 8.00 | 1.200 | 15.0 | 85.0 |
| 8.50 | 1.200 | 5.0 | 95.0 |
| 8.52 | 1.200 | 30.0 | 70.0 |
| 9.50 | 1.200 | 30.0 | 70.0 |

Run on G64 uPLC. (PC_306)

Sampling: Samples 15 μL reaction mixture diluted into 1.0 mL MeCN:water (4:1), 0.5 μL injection volume.

| Reaction | Metal Source (10 mol %) | Ligand | Ligand charge (mol %) | Additive (10 mol %) | $Et_3N$ (mol %) |
|---|---|---|---|---|---|
| 1 | Pd-113 | none | 0 | $Et_3SiH$ | 0 |
| 2 | Pd-113 | none | 0 | none | 0 |
| 3 | $Pd(OAc)_2$ | P(OH)(t-Bu)$_2$ | 20 | $Et_3SiH$ | 0 |
| 4 | $Pd(OAc)_2$ | P(OH)(t-Bu)$_2$ | 20 | none | 0 |
| 5 | Pd-113 | None | 0 | iPrCOCl | 0 |
| 6 | $Pd(dba)_2$ | P(t-Bu)$_3$•$HBF_4$ | 20 | iPrCOCl | 20 |
| 7 | $Pd(OAc)_2$ | P(t-Bu)$_3$•$HBF_4$ | 20 | $Et_3SiH$ | 20 |
| 8 | $Pd(OAc)_2$ | PCy3•$HBF_4$ | 20 | $Et_3SiH$ | 20 |
| 9 | $Pd(OAc)_2$ | P(t-Bu)$_2$(Me)•$HBF_4$ | 20 | $Et_3SiH$ | 20 |
| 10 | $Pd(OAc)_2$ | P(t-Bu)$_2$(Me)•$HBF_4$ | 20 | none | 20 |
| 11 | $Pd(dba)_2$ | P(O-(2,4-t-Bu)-Ph)$_3$ | 20 | iPrCOCl | 0 |
| 12 | $Pd(OAc)_2$ | t-Bu-Xphos | 20 | $Et_3SiH$ | 0 |
| 13 | $Pd(OAc)_2$ | Xantphos | 12 | $Et_3SiH$ | 0 |
| 14 | $Pd(dba)_2$ | Xantphos | 20 | iPrCOCl | 0 |
| 15 | $Pd(OAc)_2$ | Phanephos | 12 | $Et_3SiH$ | 0 |
| 16 | $Pd(OAc)_2$ | Ru-phos | 20 | $Et_3SiH$ | 0 |
| 17 | $Pd(OAc)_2$ | P(3,5-$CF_3$Ph)$_3$ | 20 | $Et_3SiH$ | 0 |
| 18 | $Pd(OAc)_2$ | Xantphos | 12 | none | 0 |
| 19 | $Pd(dba)_2$ | P(o-tol)$_3$ | 20 | iPrCOCl | 0 |
| 20 | $Pd(dba)_2$ | Ru-phos | 20 | iPrCOCl | 0 |
| 21 | $Pd(OAc)_2$ | Biphephos | 12 | $Et_3SiH$ | 0 |
| 22 | $Pd(OAc)_2$ | P(t-Bu)$_3$•$HBF_4$ | 20 | none | 20 |

Results

| Reaction | Conversion (%) | Desired Product (Area %) | Starting material (Area %) | Isomeric product (Area %) | Starting material - TBS (Area %) | Other peaks |
|---|---|---|---|---|---|---|
| 1 | 93.5 | 85.3 | 0.0 | 5.9 | 0.4 | 8.4 |
| 2 | 98.8 | 76.4 | 0.0 | 1.0 | 0.4 | 22.3 |
| 3 | 44.6 | 41.6 | 0.0 | 51.6 | 1.6 | 5.2 |

-continued

| Reaction | Conversion (%) | Desired Product (Area %) | Starting material (Area %) | Isomeric product (Area %) | Starting material - TBS (Area %) | Other peaks |
|---|---|---|---|---|---|---|
| 4 | 40.2 | 38.4 | 52.2 | 4.9 | 0.0 | 4.5 |
| 5 | 97.3 | 34.4 | 0.0 | 1.0 | 1.4 | 63.3 |
| 6 | 26.1 | 25.3 | 0.0 | 71.6 | 1.2 | 1.8 |
| 7 | 25.0 | 24.5 | 0.0 | 73.5 | 0.0 | 2.0 |
| 8 | 26.5 | 23.5 | 0.0 | 65.1 | 2.5 | 9.0 |
| 9 | 21.3 | 20.0 | 0.7 | 73.1 | 0.0 | 6.2 |
| 10 | 17.9 | 17.7 | 21.3 | 60.2 | 0.0 | 0.8 |
| 11 | 27.1 | 14.3 | 0.0 | 38.3 | 6.1 | 41.3 |
| 12 | 15.5 | 13.5 | 6.9 | 66.9 | 0.0 | 12.6 |
| 13 | 20.4 | 13.2 | 24.2 | 27.5 | 7.9 | 27.1 |
| 14 | 13.8 | 12.2 | 36.6 | 39.3 | 0.0 | 12.0 |
| 15 | 13.4 | 10.1 | 1.3 | 63.7 | 3.5 | 21.4 |
| 16 | 11.9 | 9.9 | 25.1 | 48.8 | 6.4 | 9.8 |
| 17 | 12.3 | 9.7 | 69.3 | 0.1 | 7.1 | 13.8 |
| 18 | 10.3 | 8.5 | 59.6 | 14.2 | 6.6 | 11.2 |
| 19 | 12.8 | 7.7 | 15.1 | 37.7 | 5.6 | 33.8 |
| 20 | 7.2 | 6.7 | 54.9 | 32.1 | 0.0 | 6.3 |
| 21 | 10.9 | 5.7 | 39.5 | 6.7 | 12.4 | 35.8 |
| 22 | 5.4 | 5.2 | 76.4 | 14.3 | 1.6 | 2.5 |

Example 3

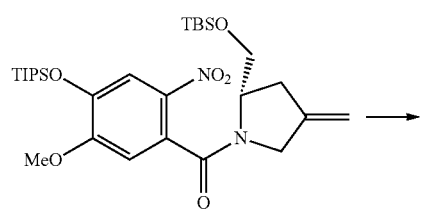

On a 100 mg scale of alkene, reactions were performed in 4 mL vials in a 24-well plate format, situated in an inerted glovebox (<10 ppm $O_2$ and <1 ppm $H_2O$). Grubbs II was weighed by hand and the vials then placed into the glovebox environment. All other solids were dispensed as solids using a Quantos weighing robot situated inside the glovebox. Stir discs were added to each vial.

Starting material (1.4 g, 1 eq.) was dissolved in dry degassed toluene (14 mL total) and 1 mL was dispensed to each vial. (100 mg/reaction and 10 mol % internal standard). Liquid additives for reactions 5 and, 6 were then added. The reactions were sealed and heated at the 70° C. for 18 hours for all reactions. Samples for uPLC/MS analysis were prepared (as below) at 30 minutes, 2 hours and 18 hours.

| Reaction Number | Catalyst | Catalyst (mol %) | Additive | Additive (mol %) | Solvent (10 vols) |
|---|---|---|---|---|---|
| 1 | Grubbs II | 5 | n-BuOH | 1000 μL | Toluene |
| 2 | Pd-113 | 5 | none | none | Toluene |
| 3 | Pd-113 | 2.5 | none | none | Toluene |
| 4 | Pd-113 | 1.25 | none | none | Toluene |
| 5 | Pd-113 | 2.5 | $Et_3SiH$ | 10 | Toluene |
| 6 | Pd-113 | 2.5 | $Et_3N$ | 20 | Toluene |
| 7 | Pd-113 | 2.5 | $PPh_3$ | 10 | Toluene |
| 8 | $(tBu_3P)_2Pd(HCl)$ | 5 | none | none | Toluene |
| 9 | $(tBu_3P)_2Pd(HCl)$ | 2.5 | none | none | Toluene |

Results at 30 Minutes

| Reaction Number | Product (Area %) | Starting Material (Area %) | Isomeric product (Area %) |
|---|---|---|---|
| 1 | 23.3 | 53.8 | 20.7 |
| 2 | 89.4 | 0.0 | 7.5 |
| 3 | 82.5 | 0.0 | 16.1 |
| 4 | 64.0 | 0.0 | 35.8 |
| 5 | 68.0 | 0.0 | 25.4 |
| 6 | 21.0 | 0.0 | 78.4 |
| 7 | 15.0 | 41.1 | 43.6 |
| 8 | 37.2 | 0.0 | 62.0 |
| 9 | 45.6 | 0.0 | 53.6 |

Results at 2 Hours

| Reaction Number | Product (Area %) | Starting Material (Area %) | Isomeric product (Area %) | Product/IS ratio |
|---|---|---|---|---|
| 1 | 45.3 | 6.9 | 47.1 | 5.5 |
| 2 | 92.4 | 0.0 | 7.6 | 12.9 |
| 3 | 90.3 | 0.0 | 8.9 | 13.0 |
| 4 | 82.9 | 0.0 | 16.8 | 11.7 |
| 5 | 88.3 | 0.0 | 10.7 | 11.7 |
| 6 | 20.7 | 0.0 | 78.8 | 2.7 |
| 7 | 15.7 | 37.7 | 46.2 | 2.3 |
| 8 | 47.1 | 0.0 | 52.5 | 7.8 |
| 9 | 57.5 | 0.0 | 42.1 | 10.0 |

Results at 18 Hours

| Reaction Number | Product (Area %) | Starting Material (Area %) | Isomeric product (Area %) | Other peaks |
|---|---|---|---|---|
| 1 | 54.2 | 0.0 | 44.1 | 1.7 |
| 2 | 89.1 | 0.0 | 6.3 | 4.5 |
| 3 | 89.2 | 0.0 | 8.2 | 2.6 |
| 4 | 82.8 | 0.0 | 16.0 | 1.2 |
| 5 | 87.2 | 0.0 | 5.5 | 7.3 |
| 6 | 20.6 | 0.0 | 78.8 | 0.6 |
| 7 | 17.1 | 32.9 | 49.7 | 0.3 |
| 8 | 59.5 | 0.0 | 40.0 | 0.5 |
| 9 | 75.0 | 0.0 | 24.7 | 0.3 |

Example 4

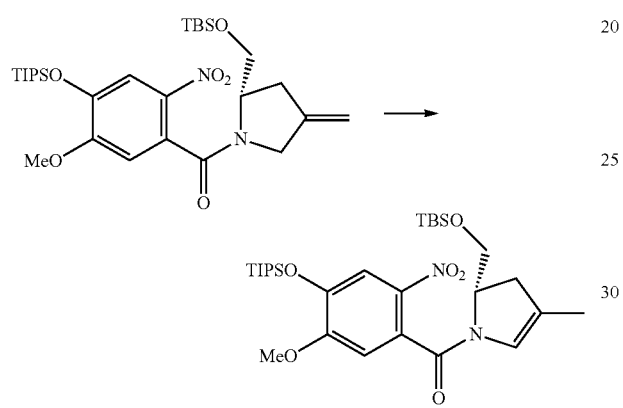

Palladium-113 (Dibromobis(tri-tert-butylphosphino)dipalladium(I)), (48 mg, 0.062 mmol, 0.07 eq) was added to a solution of the starting material (518 mg, 0.89 mmol, 1.0 eq) and triethylsilane (17.2 μL, 0.107 mmol, 0.12 eq) in anhydrous toluene (8 mL). The reaction was stirred for 2 hours at 70° C. under Argon. LC/MS showed complete conversion of starting material. Toluene was removed by rotary evaporation under reduced pressure and the residue was purified by to flash column chromatography (silica gel; isolera biotage ultra 25 g, gradient from 80/20 to 0/100 hexane/ethyl acetate v/v). Pure fractions were collected and combined and excess eluent was removed by rotary evaporation under reduced pressure to give the desired product (210 mg, 40%). Purity by LC: 90%

LCMS-B: 10.86 min; (ES+) m/z (relative intensity) 601.35 ([M+Na]$^+$, 100).

Proton NMR identical to published literature spectrum. Optical rotation within experimental error range of published literature value (−89° as compared with −100°). Chiral SFC analysis showed that the product to be enantiomerically pure.

Example 5

The starting material for this example is published as compound 16 in Gregson 2001.

Preparation of [4-[3-[4-[(2S)-2-(hydroxymethyl)-4-methyl-2,3-dihydropyrrole-1-carbonyl]-2-methoxy-5-nitro-phenoxy]propoxy]-5-methoxy-2-nitro-phenyl]-[(2S)-2-(hydroxymethyl)-4-methyl-2,3-dihydropyrrol-1-yl]methanone

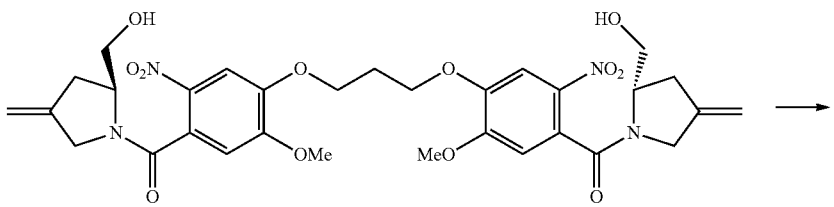

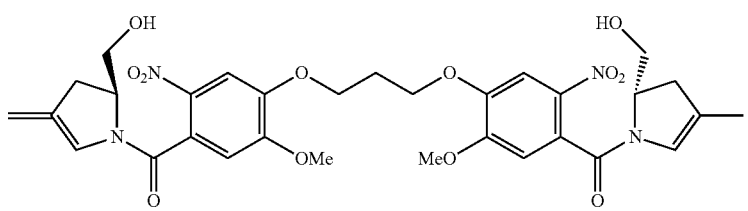

[4-[3-[4-[(2S)-2-(hydroxymethyl)-4-methylene-pyrrolidine-1-carbonyl]-2-methoxy-5-nitro-phenoxy]propoxy]-5-methoxy-2-nitro-phenyl]-[(2S)-2-(hydroxymethyl)-4-methylene-pyrrolidin-1-yl]methanone (100 mg, 0.15 mmol), and dibromobis(tri-tert-butylphosphine)dipalladium(I) (3.31 mg, 0.0004 mmol) were mixed in dry degassed toluene (1.5 mL) under an inert atmosphere. The reaction mixture was heated to 75° C. and held for 24 h. A second portion of dibromobis(tri-tert-butylphosphine)dipalladium(I) (2.95 mg, 0.0004 mmol) was added to the reaction mixture and it was held at 75° C. for a further 20 h. The reaction mixture was cooled to 20° C.

Preparation of [(2S)-1-[4-[3-[4-[(2S)-2-(acetoxymethyl)-4-methylene-pyrrolidine-1-carbonyl]-2-methoxy-5-nitro-phenoxy]propoxy]-5-methoxy-2-nitro-benzoyl]-4-methylene-pyrrolidin-2-yl]methyl acetate

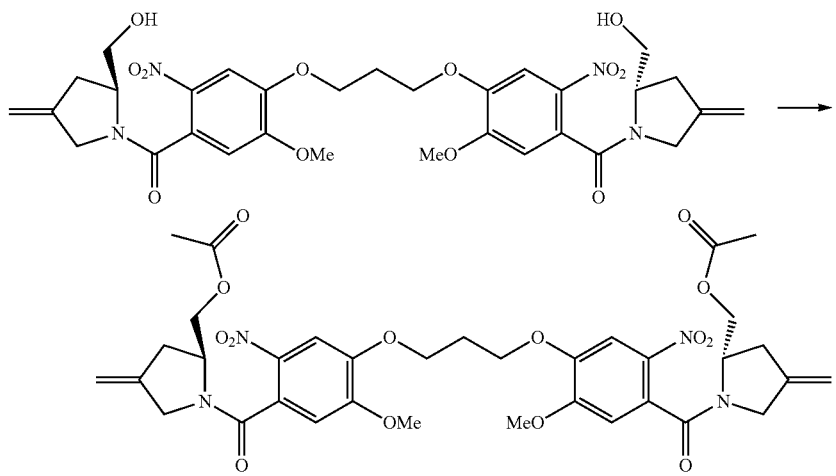

Acetic anhydride (0.72 ml, 7.61 mmol) was added to a stirred solution of [4-[3-[4-[(2S)-2-(hydroxymethyl)-4-methylene-pyrrolidine-1-carbonyl]-2-methoxy-5-nitro-phenoxy]propoxy]-5-methoxy-2-nitro-phenyl]-[(2S)-2-(hydroxymethyl)-4-methylene-pyrrolidin-1-yl]methanone (1.00 g, 1.52 mmol) and triethylamine (0.85 mL, 6.09 mmol) in 2-methyltetrahydrofuran (15 mL). The reaction mixture was held at 20° C. for 20 h. The reaction mixture was washed with water (5.0 mL) three times, and the solvent removed under vacuum. The reaction material was purified by silica chromatography to give [(2S)-1-[4-[3-[4-[(2S)-2-(acetoxymethyl)-4-methylene-pyrrolidine-1-carbonyl]-2-methoxy-5-nitro-phenoxy]propoxy]-5-methoxy-2-nitro-benzoyl]-4-methylene-pyrrolidin-2-yl]methyl acetate (0.83 g, 73.6%) as a yellow oil; $^1$H NMR (500 MHz, DMSO-$d_6$) δ ppm 1.17 (t, J=7.13 Hz, 1H) 1.86-2.07 (m, 6H) 2.27 (br t, J=5.72 Hz, 1H) 2.34-2.44 (m, 1H) 2.52-2.55 (m, 1H) 2.71-2.84 (m, 1H) 3.69-3.85 (m, 3H) 3.87-4.22 (m, 9H) 4.29 (br t, J=5.76 Hz, 3H) 4.32-4.44 (m, 1H) 4.53-4.58 (m, 1H) 4.94 (br s, 1H) 5.02 (br s, 1H) 5.07-5.12 (m, 1H) 5.12-5.17 (m, 1H) 5.76 (s, 1H) 7.07 (s, 1H) 7.23 (s, 1H) 7.73-7.77 (m, 1H).

Preparation of [(2S)-1-[4-[3-[4-[(2S)-2-(acetoxymethyl)-4-methylene-pyrrolidine-1-carbonyl]-2-methoxy-5-nitro-phenoxy]propoxy]-5-methoxy-2-nitro-benzoyl]-4-methylene-pyrrolidin-2-yl]methyl acetate

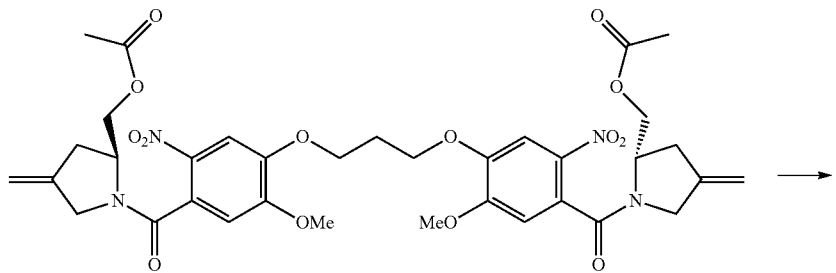

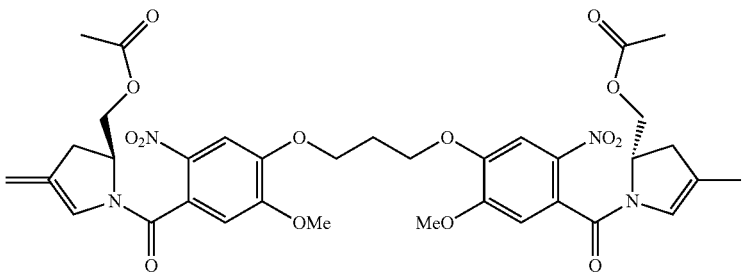

[(2S)-1-[4-[3-[4-[(2S)-2-(acetoxymethyl)-4-methylene-pyrrolidine-1-carbonyl]-2-methoxy-5-nitro-phenoxy]propoxy]-5-methoxy-2-nitro-benzoyl]-4-methylene-pyrrolidin-2-yl]methyl acetate (78.4 mg, 0.11 mmol), and dibromobis(tri-tert-butylphosphine)dipalladium(I) (2.66 mg, 0.0003 mmol) were mixed in dry degassed toluene (1.5 mL) under an inert atmosphere. The reaction mixture was heated to 75° C. and held for 44 h. A second portion of dibromobis(tri-tert-butylphosphine)dipalladium(1) (2.85 mg, 0.0004 mmol) was added to the reaction mixture and it was held at 75° C. for a further 20 h. The reaction mixture was cooled to 20° C.

Preparation of [4-[3-[4-[(2S)-2-[[tert-butyl(dimethyl)silyl]oxymethyl]-4-methylene-pyrrolidine-1-carbonyl]-2-methoxy-5-nitro-phenoxy]propoxy]-5-methoxy-2-nitro-phenyl]-[(2S)-2-[[tert-butyl(dimethyl)silyl]oxymethyl]-4-methylene-pyrrolidin-1-yl]methanone

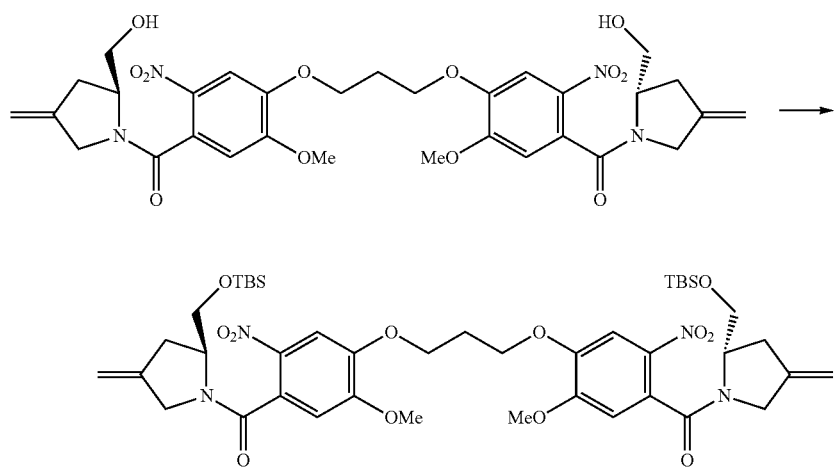

Tert-butyldimethylchlorosilane (1.18 g, 7.61 mmol) was added to a stirred solution of [4-[3-[4-[(2S)-2-(hydroxymethyl)-4-methylene-pyrrolidine-1-carbonyl]-2-methoxy-5-nitro-phenoxy]propoxy]-5-methoxy-2-nitro-phenyl]-[(2S)-2-(hydroxymethyl)-4-methylene-pyrrolidin-1-yl]methanone (1.00 g, 1.52 mmol) and triethylamine (1.28 mL, 9.14 mmol) in 2-methyltetrahydrofuran (15 mL). The reaction was heated to 50° C. and held at this temperature for 6 h. Additional triethylamine (1.28 mL, 9.14 mmol) and tert-butyldimethylchlorosilane (1.18 g, 7.61 mmol) were added to the reaction and the reaction mixture was held at 50° C. for a further 16 h. The reaction mixture was cooled to 20° C. The reaction mixture was washed with water (5.0 mL) three times, and the solvent removed under vacuum. The reaction material was purified by silica chromatography to give [4-[3-[4-[(2S)-2-[[tert-butyl(dimethyl)silyl]oxymethyl]-4-methylene-pyrrolidine-1-carbonyl]-2-methoxy-5-nitro-phenoxy]propoxy]-5-methoxy-2-nitro-phenyl]-[(2S)-2-[[tert-butyl(dimethyl)silyl]oxymethyl]-4-methylene-pyrrolidin-1-yl]methanone (0.88 g, 65.3%) as a yellow solid; $^1$H NMR (400 MHz, DMSO-$d_6$) δ ppm −0.29-0.22 (m, 6H) −0.08 (s, 1H) 0.61-0.66 (m, 10H) 0.81 (s, 17H) 1.10 (t, J=7.11 Hz, 2H) 1.91 (s, 2H) 2.11-2.27 (m, 3H) 2.34-2.40 (m, 1H) 2.44-2.53 (m, 2H) 2.55-2.73 (m, 3H) 3.15 (t, J=9.59 Hz, 1H) 3.29 (dd, J=10.18, 3.72 Hz, 1H) 3.39-3.49 (m, 2H) 3.51-3.59 (m, 1H) 3.63-3.86 (m, 16H) 3.95 (q, J=7.11 Hz, 2H) 4.16-4.31 (m, 9H) 4.83 (br s, 2H) 4.92 (br s, 2H) 5.03 (br d, J=11.53 Hz, 2H) 6.93 (s, 2H) 7.14 (s, 1H) 7.63-7.70 (m, 3H).

Preparation of [4-[3-[4-[(2S)-2-[[tert-butyl(dimethyl)silyl]oxymethyl]-4-methyl-2,3-dihydropyrrole-1-carbonyl]-2-methoxy-5-nitro-phenoxy]propoxy]-5-methoxy-2-nitro-phenyl]-[(2S)-2-[[tert-butyl(dimethyl)silyl]oxymethyl]-4-methyl-2,3-dihydropyrrol-1-yl]methanone

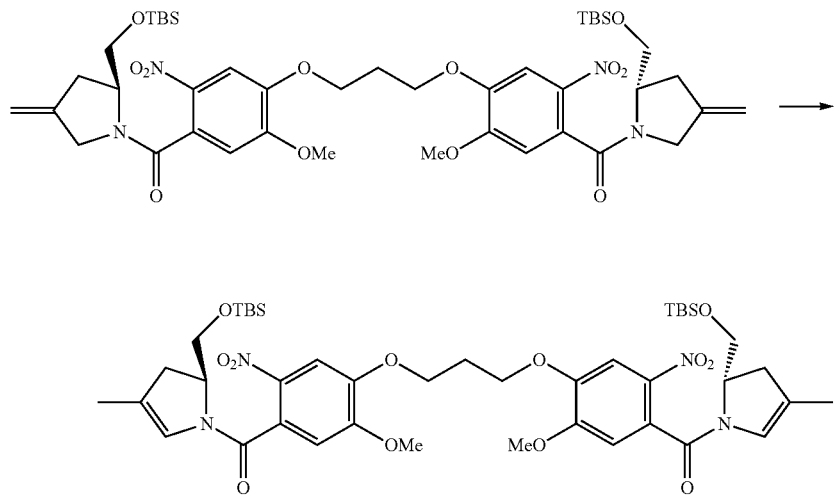

[4-[3-[4-[(2S)-2-[[tert-butyl(dimethyl)silyl]oxymethyl]-4-methylene-pyrrolidine-1-carbonyl]-2-methoxy-5-nitro-phenoxy]propoxy]-5-methoxy-2-nitro-phenyl]-[(2S)-2-[[tert-butyl(dimethyl)silyl]oxymethyl]-4-methylene-pyrrolidin-1-yl]methanone (100 mg, 0.15 mmol), and dibromobis(tri-tert-butylphosphine)dipalladium(I) (2.48 mg, 0.0003 mmol) were mixed in dry degassed toluene (1.5 mL) under an inert atmosphere. The reaction mixture was heated to 75° C. and held for 24 h. A second portion of dibromobis(tri-tert-butylphosphine)dipalladium(I) (2.41 mg, 0.0003 mmol) was added to the reaction mixture and it was held at 75° C. for a further 20 h. The reaction mixture was cooled to 20° C.

REFERENCES

| Reference | DOI |
| --- | --- |
| Tiberghien, A, et al., ACS Med. Chem. Lett. 2016, 7, 983-987 | 10.1021/acsmedchemlett.6b00062 |
| Kitamura, T, et al., Tetrahedron 2004, 60, 9649-9657 | 10.1016/j.tet.2004.07.040 |
| Wuts, P & Greene, T, Greene's Protective Groups in Organic Synthesis, Fourth Edition (Wiley-Interscience), 2007 | 10.1002/0470053488 |
| Gregson, S. J., et al., J Med Chem, 2001, 44, 737-748 | 10.1021/jm001064n |

STATEMENTS OF INVENTION

1. A method of synthesising a compound of formula I:

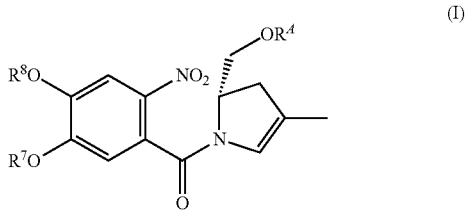

from a compound of formula II:

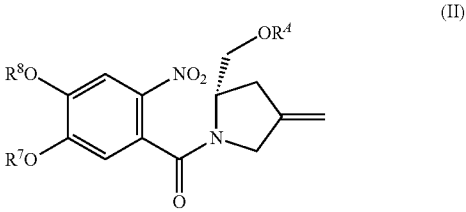

where
R$^A$ is either H or Prot$^{O1}$;
R$^8$ is either:
(i) Prot$^{O3}$; or
(ii) a group of formula A1 in formula (I) and A2 in formula (II):

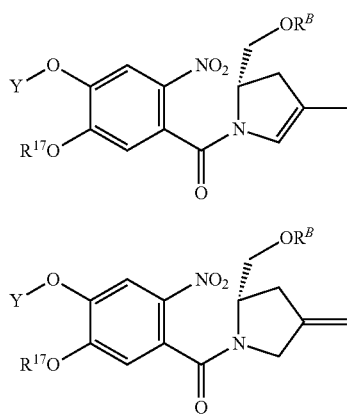

where R$^B$ is either H or Prot$^{O2}$;
R$^7$ is selected from C$_{1-4}$ alkyl and benzyl;
R$^{17}$ is selected from C$_{1-4}$ alkyl and benzyl;
Y is a C$_{3-12}$ alkylene group, which chain may be interrupted by one or more heteroatoms, selected from O, S and NR$^{N2}$ (where R$^{N2}$ is H or C$_{1-4}$ alkyl), or an aromatic ring selected from benzene and pyridine;
Prot$^{O1}$, Prot$^{O2}$ and Prot$^{O3}$ are independently hydroxyl protecting groups which are not labile under the reaction conditions.

2. A method according to statement 1, wherein R$^7$ is a C$_{1-4}$ alkyl group.

3. A method according to statement 2, wherein R$^7$ is methyl.

4. A method according to statement 2, wherein R$^7$ is ethyl.

5. A method according to statement 1, wherein R$^7$ is benzyl.

6. A method according to any one of statements 1 to 5, wherein R$^A$ is Prot$^{O1}$.

7. A method according to any one of statements 1 to 5, wherein R$^A$ is H.

8. A method according to any one of statements 1 to 6, wherein Prot$^{O1}$ is selected from substituted methyl ethers, substituted ethyl ethers (except those containing unsaturation), methoxy substituted benzyl ethers, silyl ethers and acetates.

9. A method according to statement 8, wherein Prot$^{O1}$ is selected from:
(a) methoxymethyl (MOM), β-methoxyethoxymethyl ether (MEM), benzyloxymethyl, t-butoxymethyl and siloxymethyl;
(b) 1-ethoxyethyl, 2-hydroxyethyl, 1-[2-(trimethylsilyl)ethoxy]ethyl, 2,2,2-trichloroethyl, 2-trimethylsilylethyl and t-butyl;
(c) p-methoxy-benzyl, dimethoxybenzyl and nitrobenzyl;
(d) trimethylsilyl (TMS), triethylsilyl (TES), tert-butyldimethylsilyl (TBS), tert-butyldiphenylsilyl (TBDPS) and triisopropylsilyl ether (TIPS);
(e) chloroacetate, methoxyacetate, phenoxyacetate and benzoate.

10. A method according to statement 8, wherein Prot$^{O1}$ is a silyl ether.

11. A method according to statement 10, wherein Prot$^{O1}$ is tert-butyldimethylsilyl (TBS).

12. A method according to any one of statements 1 to 11, wherein R$^8$ is Prot$^{O3}$.

13. A method according to statement 12, wherein R$^8$ is selected from substituted methyl ethers, substituted ethyl ethers (except those containing unsaturation), methoxy substituted benzyl ethers, silyl ethers and acetates.

14. A method according to statement 13, wherein R$^8$ is selected from:
(a) methoxymethyl (MOM), β-methoxyethoxymethyl ether (MEM), benzyloxymethyl, t-butoxymethyl and siloxymethyl;
(b) 1-ethoxyethyl, 2-hydroxyethyl, 1-[2-(trimethylsilyl)ethoxy]ethyl, 2,2,2-trichloroethyl, 2-trimethylsilylethyl and t-butyl;
(c) p-methoxy-benzyl, dimethoxybenzyl and nitrobenzyl;
(d) trimethylsilyl (TMS), triethylsilyl (TES), tert-butyldimethylsilyl (TBS), tert-butyldiphenylsilyl (TBDPS) and triisopropylsilyl ether (TIPS);
(e) chloroacetate, methoxyacetate, phenoxyacetate and benzoate.

15. A method according to statement 13, wherein R$^8$ is a silyl ether.

16. A method according to statement 15, wherein R$^8$ is triisopropylsilyl ether (TIPS).

17. A method according to any one of statements 1 to 11, wherein R$^8$ is a group of formula A1 in formula (I) and A2 in formula (II).

18. A method according to statement 17, wherein R$^{17}$ is a C$_{1-4}$ alkyl group.

19. A method according to statement 18, wherein R$^{17}$ is methyl.

20. A method according to statement 18, wherein R$^{17}$ is ethyl.

21. A method according to statement 17, wherein R$^{17}$ is benzyl.

22. A method according to any one of statements 17 to 21, wherein Y is a C$_{3-12}$ alkylene group which is not interrupted.

23. A method according to statement 22, wherein Y is —(CH$_2$)$_n$—, where n is an integer from 3 to 12.

24. A method according to statement 23, wherein Y is selected from —(CH$_2$)$_3$— and —(CH$_2$)$_5$—.

25. A method according to any one of statements 17 to 21, wherein Y is a C$_{3-12}$ alkylene group which is interrupted by an aromatic ring.

26. A method according to statement 25, wherein Y is:

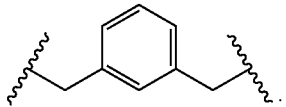

27. A method according to any one of statements 17 to 26, wherein R$^B$ is Prot$^{O2}$.

28. A method according to any one of statements 17 to 26, wherein R$^B$ is H.

29. A method according to any one of statements 17 to 27, wherein Prot$^{O2}$ is selected from substituted methyl ethers, substituted ethyl ethers (except those containing unsaturation), methoxy substituted benzyl ethers, silyl ethers and acetates.

30. A method according to statement 29, wherein Prot$^{O2}$ is selected from:
(a) methoxymethyl (MOM), β-methoxyethoxymethyl ether (MEM), benzyloxymethyl, t-butoxymethyl and siloxymethyl;
(b) 1-ethoxyethyl, 2-hydroxyethyl, 1-[2-(trimethylsilyl)ethoxy]ethyl, 2,2,2-trichloroethyl, 2-trimethylsilylethyl and t-butyl;
(c) p-methoxy-benzyl, dimethoxybenzyl and nitrobenzyl;
(d) trimethylsilyl (TMS), triethylsilyl (TES), tert-butyldimethylsilyl (TBS), tert-butyldiphenylsilyl (TBDPS) and triisopropylsilyl ether (TIPS);
(e) chloroacetate, methoxyacetate, phenoxyacetate and benzoate.
31. A method according to statement 29, wherein Prot$^{O2}$ is a silyl ether.
32. A method according to statement 29, wherein Prot$^{O2}$ is tert-butyldimethylsilyl (TBS).
33. A method according to any one of statements 1 to 31, which is carried out using a catalyst, with the optional addition of an additive.
34. A method according to statement 33, wherein the catalyst comprises a metal hydride, or is able to form a metal hydride in situ.
35. A method according to statement 34, wherein the catalyst contains a transition metal, selected from Ru, Ir, Rh and Pd.
36. A method according to statement 35, wherein the transition metal is Pd.
37. A method according to statement 35, wherein the transition metal is Ru.
38. A method according to statement 35, wherein the transition metal is Rh.
39. A method according to statement 35, wherein the transition metal is Ir.
40. A method according to any one of statements 33 to 39, wherein catalyst comprises P-ligands, selected from (t-Butyl)$_3$P and Ph$_3$P.
41. A method according to statement 34, wherein the catalyst is able to form an active species comprising PdH(PR$^P_3$)X, where each R$^P$ is independently selected from t-butyl and phenyl, and X is halo.
42. A method according to statement 34, wherein the catalyst is selected from: Grubbs I; Grubbs II; Crabtrees Catalyst; RuHCl(CO)PPh$_3$; RhH(CO)PPh$_3$; Rh(COD)$_2$BF$_4$; Pd-113; Pd-118; Cationic CpRu(Pr$_3$) and (tBu$_3$P)$_2$Pd(HCl).
43. A method according to statement 42, wherein the catalyst is selected from Pd-113 and ((tBu)$_3$P)$_2$Pd(HCl).
44. A method according to statement 43, wherein the catalyst is Pd-113.
45. A method according to statement 34, wherein the catalyst is formed in situ by a metal source and appropriate ligands, wherein the metal source is selected from: Pd(OAc)$_2$ and Pd(dba)$_2$; and the appropriate ligands are selected from: P(OH)(t-Bu)$_2$; P(t-Bu)$_3$.HBF$_4$; PCy$_3$.HBF$_4$; P(t-Bu)$_2$(Me).HBF$_4$; P(O-(2,4-t-Bu)-Ph)$_3$; Xantphos; Phanephos; Ru-phos; P(o-tol)$_3$; and Biphephos.
46. A method according to any one of statements 33 to 45, wherein the optional additive is selected from:
(a) a compound suitable to generate a metal hydride in situ in combination with the catalyst;
(b) a base;
(c) an additional ligand for the catalyst.
47. A method according to statement 46, wherein the compounds suitable to generate a metal hydride in situ in combination with the catalyst is selected from Et$_3$SiH, iPrCOCl and n-BuOH.

48. A method according to statement 46, wherein the base is Et$_3$N.
49. A method according to statement 46, wherein the additional ligand for the catalyst is selected from PPh$_3$ and P(t-Bu)$_3$.
50. A method according to any one of statements 1 to 49, wherein the reaction is carried out in toluene.
51. A method according to any one of statements 1 to 50, wherein the reaction temperature is between 5 and 120° C.
52. A method according to any one of statements 1 to 51, wherein the reaction time is between half an hour and 48 hours.
53. A method according to any one of statements 1 to 52, wherein the catalyst is added in a relative amount to the starting compound of formula (II) of 1 mol % to 30 mol %.
54. A method according to any one of statements 1 to 53, wherein the reaction is carried out under a substantially inert atmosphere.
55. A method according to statement 54, wherein the substantially inert atmosphere is comprised predominantly of nitrogen.
56. A method according to statement 54, wherein the substantially inert atmosphere is comprised predominantly of argon.
57. A method according to any one of statements 54 to 56, wherein the substantially inert atmosphere comprises less than 10 ppm of oxygen.
58. A compound of formula IIa:

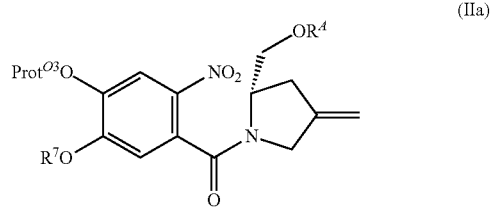

(IIa)

where R$^7$ is selected from C$_{1-4}$ alkyl and benzyl; and
R$^A$ is H or Prot$^{O1}$;
Prot$^{O1}$ and Prot$^{O3}$ are independently hydroxyl protecting groups which are not labile under the reaction conditions of the first aspect of the invention.
59. A compound according to statement 58, wherein R$^7$ is a C$_{1-4}$ alkyl group.
60. A compound according to statement 59, wherein R$^7$ is methyl.
61. A compound according to statement 59, wherein R$^7$ is ethyl.
62. A compound according to statement 58, wherein R$^7$ is benzyl.
63. A compound according to any one of statements 58 to 62, wherein R$^A$ is Prot$^{O1}$.
64. A compound according to any one of statements 58 to 62, wherein R$^A$ is H.
65. A compound according to any one of statements 58 to 63, wherein Prot$^{O1}$ is selected from substituted methyl ethers, substituted ethyl ethers (except those containing unsaturation), methoxy substituted benzyl ethers, silyl ethers and acetates.
66. A compound according to statement 65, wherein Prot$^{O1}$ is selected from:
(a) methoxymethyl (MOM), β-methoxyethoxymethyl ether (MEM), benzyloxymethyl, t-butoxymethyl and siloxymethyl;

(b) 1-ethoxyethyl, 2-hydroxyethyl, 1-[2-(trimethylsilyl)ethoxy]ethyl, 2,2,2-trichloroethyl, 2-trimethylsilylethyl and t-butyl;
(c) p-methoxy-benzyl, dimethoxybenzyl and nitrobenzyl;
(d) trimethylsilyl (TMS), triethylsilyl (TES), tert-butyldimethylsilyl (TBS), tert-butyldiphenylsilyl (TBDPS) and triisopropylsilyl ether (TIPS);
(e) chloroacetate, methoxyacetate, phenoxyacetate and benzoate.

66. A compound according to statement 65, wherein $Prot^{O1}$ is a silyl ether.

67. A compound according to statement 67, wherein $Prot^{O1}$ is tert-butyldimethylsilyl (TBS).

68. A compound according to any one of statements 58 to 67, wherein $Prot^{O3}$ is selected from substituted methyl ethers, substituted ethyl ethers (except those containing unsaturation), methoxy substituted benzyl ethers, silyl ethers and acetates.

69. A compound according to statement 68, wherein $Prot^{O3}$ is selected from:
(a) methoxymethyl (MOM), β-methoxyethoxymethyl ether (MEM), benzyloxymethyl, t-butoxymethyl and siloxymethyl;
(b) 1-ethoxyethyl, 2-hydroxyethyl, 1-[2-(trimethylsilyl)ethoxy]ethyl, 2,2,2-trichloroethyl, 2-trimethylsilylethyl and t-butyl;
(c) p-methoxy-benzyl, dimethoxybenzyl and nitrobenzyl;
(d) trimethylsilyl (TMS), triethylsilyl (TES), tert-butyldimethylsilyl (TBS), tert-butyldiphenylsilyl (TBDPS) and triisopropylsilyl ether (TIPS);
(e) chloroacetate, methoxyacetate, phenoxyacetate and benzoate.

70. A compound according to statement 68, wherein $Prot^{O3}$ is a silyl ether.

71. A compound according to statement 70, wherein $Prot^{O3}$ is triisopropylsilyl ether (TIPS).

The invention claimed is:

1. A method of synthesising a compound of formula I:

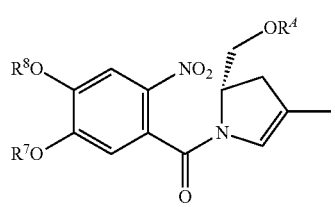
(I)

from a compound of formula II:

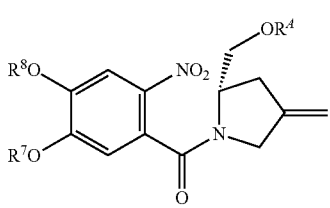
(II)

where
$R^A$ is either H or $Prot^{O1}$;
$R^8$ is either:
(i) $Prot^{O3}$; or
(ii) a group of formula A1 in formula (I) and A2 in formula (II):

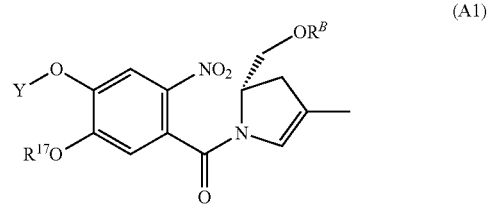
(A1)

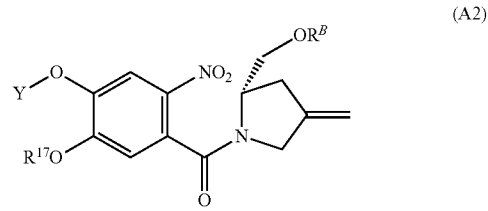
(A2)

where $R^B$ is either H or $Prot^{O2}$;
$R^7$ is selected from $C_{1-4}$ alkyl and benzyl;
$R^{17}$ is selected from $C_{1-4}$ alkyl and benzyl;
Y is a $C_{3-12}$ alkylene group, which chain may be interrupted by one or more heteroatoms, selected from O, S and $NR^{N2}$ (where $R^{N2}$ is H or C1-4 alkyl), or an aromatic ring selected from benzene and pyridine; and
$Prot^{O1}$, $Prot^{O2}$ and $Prot^{O3}$ are independently hydroxyl protecting groups which are not labile under the reaction conditions.

2. A method according to claim 1, wherein $R^7$ is selected from methyl and benzyl.

3. A method according to claim 1, wherein $R^A$ is H.

4. A method according to claim 1, wherein $R^A$ is $Prot^{O1}$, and $Prot^{O1}$ is selected from substituted methyl ethers, substituted ethyl ethers except those containing unsaturation, methoxy substituted benzyl ethers, silyl ethers, and acetates; optionally wherein $Prot^{O1}$ is tert-butyldimethylsilyl (TBS).

5. A method according to claim 1, wherein $R^8$ is $Prot^{O3}$, and is selected from substituted methyl ethers, substituted ethyl ethers except those containing unsaturation, methoxy substituted benzyl ethers, silyl ethers, and acetates; optionally wherein $R^8$ is triisopropylsilyl ether (TIPS).

6. A method according to claim 1, wherein $R^8$ is a group of formula A1 in formula (I) and A2 in formula (II).

7. A method according to claim 6, wherein $R^{17}$ is selected from methyl and benzyl.

8. A method according to claim 6, wherein Y is selected from:
(a) —$(CH_2)_3$—;
(b) —$(CH_2)_5$—; and (c)
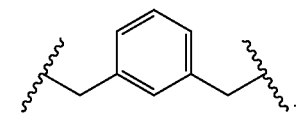
.

9. A method according to claim 6, wherein $R^B$ is H.

10. A method according to claim 6, wherein $R^B$ is $Prot^{O2}$, and $Prot^{O2}$ is selected from substituted methyl ethers, substituted ethyl ethers except those containing unsaturation, methoxy substituted benzyl ethers, silyl ethers, and acetates; optionally wherein $Prot^{O2}$ is tert-butyldimethylsilyl (TBS).

11. A method according to claim 1, which is carried out using a catalyst, with the optional addition of an additive.

12. A method according to claim 11, wherein the catalyst:
a) comprises a metal hydride, or is able to form a metal hydride in situ;
b) contains a transition metal selected from Ru, Ir, Rh and Pd;
c) comprises P-ligands selected from (t-Butyl)$_3$P and Ph$_3$P
d) is able to form an active species comprising PdH(PR$^P_3$)X, where each R$^P$ is independently selected from t-butyl and phenyl, and X is halo;
e) is selected from: Grubbs I; Grubbs II; Crabtrees Catalyst; RuHCl(CO)PPh$_3$; RhH(CO)PPh$_3$; Rh(COD)$_2$BF$_4$; Pd-113; Pd-118; Cationic CpRu(Pr$_3$) and (tBu$_3$P)$_2$Pd(HCl);
f) is formed in situ by a metal source and appropriate ligands, wherein the metal source is selected from: Pd(OAc)$_2$ and Pd(dba)$_2$; and the appropriate ligands are selected from: P(OH)(t-Bu)$_2$; P(t-Bu)$_3$.HBF$_4$; PCy$_3$.HBF$_4$; P(t-Bu)$_2$(Me).HBF$_4$; P(O-(2,4-t-Bu)-Ph)$_3$; Xantphos; Phanephos; Ru-phos; P(o-tol)$_3$; and Biphephos.

13. A method according to claim 11, wherein the optional additive is selected from:
(a) a compound suitable to generate a metal hydride in situ in combination with the catalyst;
(b) a base; and
(c) an additional ligand for the catalyst.

14. A method according to claim 1, where the reaction is carried out under a substantially inert atmosphere selected from:
(a) an atmosphere comprising predominantly of nitrogen;
(b) an atmosphere comprising predominantly of argon;
(c) an atmosphere comprising predominantly of nitrogen or argon, and less than 10 ppm of oxygen.

15. A compound of formula IIa:

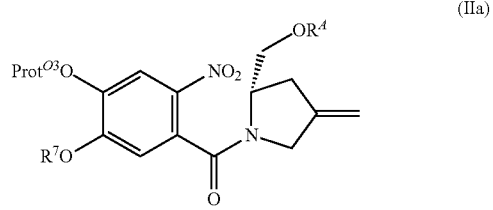

where $R^7$ is selected from $C_{1-4}$ alkyl and benzyl;
$R^A$ is H or $Prot^{O1}$; and
$Prot^{O1}$ is a hydroxyl protecting group which is not labile under the reaction conditions of the first aspect of the invention; and $Prot^{O3}$ is selected from:
(a) methoxymethyl (MOM), β-methoxyethoxymethyl ether (MEM), benzyloxymethyl, t-butoxymethyl and siloxymethyl;
(b) 1-ethoxyethyl, 2-hydroxyethyl, 1-[2-(trimethylsilyl)ethoxy]ethyl, 2,2,2-trichloroethyl, 2-trimethylsilylethyl and t-butyl;
(c) p-methoxy-benzyl, dimethoxybenzyl and nitrobenzyl;
(d) trimethylsilyl (TMS), triethylsilyl (TES), tert-butyldimethylsilyl (TBS), tert-butyldiphenylsilyl (TBDPS) and triisopropylsilyl ether (TIPS); and
(e) chloroacetate, methoxyacetate, phenoxyacetate and benzoate.

16. A compound according to claim 15 wherein $R^7$ is selected from methyl and benzyl.

17. A compound according to claim 15, wherein $Prot^{O1}$ is selected from substituted methyl ethers, substituted ethyl ethers except those containing unsaturation, methoxy substituted benzyl ethers, silyl ethers, and acetates; optionally wherein $Prot^{O1}$ is tert-butyldimethylsilyl (TBS).

18. A compound according to claim 17, wherein $Prot^{O3}$ is triisopropylsilyl ether (TIPS).

* * * * *